(12) United States Patent
Glenn, Jr. et al.

(10) Patent No.: US 8,461,091 B2
(45) Date of Patent: *Jun. 11, 2013

(54) PERSONAL CARE COMPOSITION IN THE FORM OF AN ARTICLE HAVING A POROUS, DISSOLVABLE SOLID STRUCTURE

(75) Inventors: Robert Wayne Glenn, Jr., Liberty Township, OH (US); James Merle Heinrich, Fairfield, OH (US); Kathleen Mary Kaufman, Cincinnati, OH (US); Darren Paul Trokhan, Hamilton, OH (US); Thomas Edward Dufresne, Morrow, OH (US); Julie Masters Lubbers, Fort Thomas, KY (US); Renee Danielle Bolden, Hamilton, OH (US); Lee Arnold Schechtman, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/633,301

(22) Filed: Dec. 8, 2009

(65) Prior Publication Data
US 2010/0286011 A1 Nov. 11, 2010

Related U.S. Application Data

(60) Provisional application No. 61/120,765, filed on Dec. 8, 2008.

(51) Int. Cl.
| | |
|---|---|
| *C11D 17/00* | (2006.01) |
| *C11D 1/12* | (2006.01) |
| *C11D 1/14* | (2006.01) |
| *C11D 1/29* | (2006.01) |
| *C11D 1/88* | (2006.01) |
| *C11D 1/90* | (2006.01) |
| *A61K 8/02* | (2006.01) |

(52) U.S. Cl.
USPC ........... 510/120; 510/123; 510/127; 510/130; 510/141; 510/155; 510/156; 510/445; 510/475; 510/495; 510/501; 510/503; 424/400

(58) Field of Classification Search
USPC ................ 510/120, 123, 127, 130, 141, 155, 510/156, 445, 475, 495, 501, 503; 424/400
See application file for complete search history.

(56) References Cited

U.S. PATENT DOCUMENTS

| | | |
|---|---|---|
| 2,356,168 A | 8/1944 | Mabley |
| 2,396,278 A | 3/1946 | Lind |

(Continued)

FOREIGN PATENT DOCUMENTS

| | | |
|---|---|---|
| CN | 1138091 A | 12/1996 |
| CN | 1219388 A | 6/1999 |

(Continued)

OTHER PUBLICATIONS

U.S. Appl. No. 13/440,475, filed Apr. 5, 2012, Glenn, Jr.

(Continued)

*Primary Examiner* — Lorna M Douyon
(74) *Attorney, Agent, or Firm* — Angela K. Haughey

(57) ABSTRACT

The present invention relates to a dissolvable article in the form of a porous dissolvable solid structure, comprising from about 10% to about 50% water soluble polymer; from about 1% to about 25% plasticizer; from about 23% to about 75% surfactant; wherein the surfactants comprise one or more surfactants from Group I, wherein Group I includes anionic surfactants, and one or more surfactants from Group II, wherein Group II includes a surfactant selected from the group consisting of amphoteric, zwitterionic and combinations thereof; wherein the ratio of Group I to Group II surfactants is from about 5:95 to about 30:70; and wherein the dissolvable article has a density of from about 0.05 g/cm3 to about 0.40 g/cm3.

28 Claims, 7 Drawing Sheets

Interior Volume

Full Volume

U.S. PATENT DOCUMENTS

| | | | |
|---|---|---|---|
| 2,438,091 A | 3/1948 | Lynch | |
| 2,486,921 A | 11/1949 | Byerly | |
| 2,486,922 A | 11/1949 | Strain | |
| 2,528,378 A | 10/1950 | Mannheimer | |
| 2,658,072 A | 11/1953 | Kosmin | |
| 2,809,971 A | 10/1957 | Bernstein | |
| 3,152,046 A | 10/1964 | Kapral | |
| 3,236,733 A | 2/1966 | Karsten | |
| 3,321,425 A | 5/1967 | Blau | |
| 3,332,880 A | 7/1967 | Kessler | |
| 3,426,440 A | 2/1969 | Shen | |
| 3,489,688 A | 1/1970 | Pospischil | |
| 3,653,383 A | 4/1972 | Wise | |
| 3,695,989 A | 10/1972 | Albert | |
| 3,753,196 A | 8/1973 | Kurtz | |
| 3,761,418 A | 9/1973 | Parran, Jr. | |
| 3,929,678 A | 12/1975 | Laughlin | |
| 3,967,921 A | 7/1976 | Haberli | |
| 4,020,156 A | 4/1977 | Murray | |
| 4,051,081 A | 9/1977 | Jabs | |
| 4,089,945 A | 5/1978 | Brinkman | |
| 4,196,190 A | 4/1980 | Gehman et al. | |
| 4,197,865 A | 4/1980 | Jacquet | |
| 4,217,914 A | 8/1980 | Jacquet | |
| 4,272,511 A | 6/1981 | Papantoniou | |
| 4,323,683 A | 4/1982 | Bolich, Jr. | |
| 4,345,080 A | 8/1982 | Bolich, Jr. | |
| 4,379,753 A | 4/1983 | Bolich, Jr. | |
| 4,381,919 A | 5/1983 | Jacquet | |
| 4,422,853 A | 12/1983 | Jacquet | |
| 4,470,982 A | 9/1984 | Winkler | |
| 4,507,280 A | 3/1985 | Pohl | |
| 4,529,586 A | 7/1985 | De Marco | |
| 4,565,647 A | 1/1986 | Llenado | |
| 4,663,158 A | 5/1987 | Wolfram | |
| 4,710,374 A | 12/1987 | Grollier | |
| 4,822,613 A | 4/1989 | Rodero | |
| 4,885,107 A | 12/1989 | Wetzel | |
| 4,976,953 A | 12/1990 | Orr | |
| 4,990,280 A | 2/1991 | Thorengaard | |
| 5,055,384 A | 10/1991 | Kuhnert | |
| 5,061,481 A | 10/1991 | Suzuki | |
| 5,062,889 A | 11/1991 | Hohl | |
| 5,094,853 A | 3/1992 | Hagerty | |
| 5,100,658 A | 3/1992 | Bolich, Jr. | |
| 5,104,646 A | 4/1992 | Bolich, Jr. et al. | |
| 5,106,609 A | 4/1992 | Bolich, Jr. | |
| 5,166,276 A | 11/1992 | Hayama | |
| 5,220,033 A | 6/1993 | Kamei | |
| 5,280,079 A | 1/1994 | Allen | |
| RE34,584 E | 4/1994 | Grote | |
| 5,391,368 A | 2/1995 | Gerstein | |
| 5,409,703 A | 4/1995 | McAnalley | |
| 5,429,628 A | 7/1995 | Trinh | |
| 5,457,895 A | 10/1995 | Thompson | |
| 5,476,597 A | 12/1995 | Sakata | |
| 5,580,481 A | 12/1996 | Sakata | |
| 5,582,786 A | 12/1996 | Brunskill | |
| 5,660,845 A | 8/1997 | Trinh | |
| 5,672,576 A | 9/1997 | Behrens | |
| 5,674,478 A | 10/1997 | Dodd | |
| 5,750,122 A | 5/1998 | Evans | |
| 5,780,047 A | 7/1998 | Kamiya | |
| 5,955,419 A | 9/1999 | Barket, Jr. | |
| 6,010,719 A | 1/2000 | Remon | |
| 6,106,849 A | 8/2000 | Malkan | |
| 6,177,391 B1 | 1/2001 | Zafar | |
| 6,200,949 B1 | 3/2001 | Reijmer | |
| 6,458,754 B1 | 10/2002 | Velaquez | |
| 6,503,521 B1 | 1/2003 | Atis | |
| 6,790,814 B1 | 9/2004 | Marin | |
| 6,846,784 B2 | 1/2005 | Engel | |
| 6,943,200 B1 | 9/2005 | Corrand | |
| 7,015,181 B2 * | 3/2006 | Lambino | 510/141 |
| 7,285,520 B2 | 10/2007 | Krzysik | |
| 7,901,696 B2 | 3/2011 | Eknoian | |
| 2002/0064510 A1 * | 5/2002 | Dalrymple et al. | 424/70.22 |
| 2002/0077264 A1 | 6/2002 | Roberts | |
| 2002/0081930 A1 | 6/2002 | Jackson | |
| 2002/0098994 A1 | 7/2002 | Zafar | |
| 2002/0099109 A1 | 7/2002 | Dufton | |
| 2002/0177621 A1 | 11/2002 | Hanada | |
| 2002/0187181 A1 | 12/2002 | Godbey | |
| 2003/0032573 A1 | 2/2003 | Tanner | |
| 2003/0045441 A1 | 3/2003 | Hsu | |
| 2003/0069154 A1 | 4/2003 | Hsu | |
| 2003/0080150 A1 | 5/2003 | Cowan | |
| 2003/0099691 A1 | 5/2003 | Lydzinski | |
| 2003/0099692 A1 | 5/2003 | Lydzinski | |
| 2003/0180242 A1 * | 9/2003 | Eccard et al. | 424/70.11 |
| 2003/0186826 A1 * | 10/2003 | Eccard et al. | 510/130 |
| 2003/0194416 A1 | 10/2003 | Shefer | |
| 2003/0199412 A1 | 10/2003 | Gupta | |
| 2003/0207776 A1 | 11/2003 | Shefer | |
| 2003/0215522 A1 | 11/2003 | Johnson | |
| 2003/0232183 A1 | 12/2003 | Dufton | |
| 2004/0029762 A1 | 2/2004 | Hensley | |
| 2004/0032859 A1 | 2/2004 | Mino | |
| 2004/0048759 A1 | 3/2004 | Ribble | |
| 2004/0053808 A1 | 3/2004 | Raehse | |
| 2004/0071742 A1 | 4/2004 | Popplewell | |
| 2004/0071755 A1 | 4/2004 | Fox | |
| 2004/0108615 A1 | 6/2004 | Foley | |
| 2004/0110656 A1 * | 6/2004 | Casey et al. | 510/424 |
| 2004/0126585 A1 | 7/2004 | Kerins | |
| 2004/0175404 A1 | 9/2004 | Shefer | |
| 2004/0202632 A1 * | 10/2004 | Gott et al. | 424/70.13 |
| 2004/0206270 A1 | 10/2004 | Vanmaele | |
| 2004/0242772 A1 | 12/2004 | Huth | |
| 2005/0069575 A1 | 3/2005 | Fox | |
| 2005/0136780 A1 | 6/2005 | Clark | |
| 2005/0137272 A1 | 6/2005 | Gaserod | |
| 2005/0202992 A1 | 9/2005 | Grandio Portabales et al. | |
| 2005/0232954 A1 * | 10/2005 | Yoshinari et al. | 424/400 |
| 2005/0272836 A1 | 12/2005 | Yaginuma | |
| 2005/0287106 A1 | 12/2005 | Legendre | |
| 2006/0002880 A1 * | 1/2006 | Peffly et al. | 424/70.13 |
| 2006/0052263 A1 | 3/2006 | Roreger | |
| 2006/0228319 A1 | 10/2006 | Vona | |
| 2007/0028939 A1 | 2/2007 | Mareri | |
| 2007/0149435 A1 | 6/2007 | Koenig | |
| 2007/0225388 A1 | 9/2007 | Cooper et al. | |
| 2008/0035174 A1 | 2/2008 | Aubrun-Sonneville | |
| 2008/0090939 A1 | 4/2008 | Netravali | |
| 2008/0131695 A1 | 6/2008 | Aouad | |
| 2008/0138492 A1 | 6/2008 | Cingotti | |
| 2008/0152894 A1 | 6/2008 | Beihoffer | |
| 2008/0215023 A1 | 9/2008 | Scavone | |
| 2008/0293839 A1 | 11/2008 | Stobby | |
| 2009/0232873 A1 * | 9/2009 | Glenn et al. | 424/443 |
| 2009/0263342 A1 * | 10/2009 | Glenn et al. | 424/70.11 |
| 2010/0167971 A1 | 7/2010 | Glenn, Jr. | |
| 2010/0173817 A1 | 7/2010 | Glenn, Jr. | |
| 2010/0179083 A1 | 7/2010 | Glenn, Jr. | |
| 2010/0279905 A1 | 11/2010 | Glenn, Jr. | |
| 2010/0291165 A1 | 11/2010 | Glenn, Jr. | |
| 2010/0298188 A1 | 11/2010 | Glenn, Jr. | |
| 2011/0023240 A1 | 2/2011 | Fossum | |
| 2011/0028373 A1 | 2/2011 | Fossum | |
| 2011/0028374 A1 | 2/2011 | Fossum | |
| 2011/0182956 A1 | 7/2011 | Glenn, Jr. | |
| 2011/0189246 A1 | 8/2011 | Glenn, Jr. | |
| 2011/0189247 A1 | 8/2011 | Glenn, Jr. | |
| 2011/0195098 A1 | 8/2011 | Glenn, Jr. | |
| 2012/0021026 A1 | 1/2012 | Glenn, Jr. | |

FOREIGN PATENT DOCUMENTS

| | | | |
|---|---|---|---|
| CN | 1268558 A | 10/2000 | |
| CN | 1357613 A | 7/2002 | |
| CN | 1530431 A | 9/2004 | |
| CN | 1583991 A | 2/2005 | |
| DE | 19607851 A1 | 9/1997 | |
| DE | 10331767 A1 | 2/2005 | |
| EP | 609808 A1 | 8/1994 | |
| EP | 0858828 A1 | 8/1998 | |
| EP | 1160311 B1 | 12/2001 | |
| EP | 1217987 B1 | 12/2004 | |

| | | | |
|---|---|---|---|
| EP | 2085434 A1 | 8/2009 |
| FR | 2871685 A | 12/2005 |
| FR | 2886845 A | 12/2006 |
| GB | 2235204 A | 2/1991 |
| GB | 2355008 A | 4/2001 |
| JP | 58021608 A | 2/1983 |
| JP | 58216109 A | 12/1983 |
| JP | 62072609 A | 4/1987 |
| JP | 62072610 A | 4/1987 |
| JP | 1313418 A | 12/1989 |
| JP | 5344873 A | 12/1993 |
| JP | 6017083 A | 1/1994 |
| JP | 7089852 A | 4/1995 |
| JP | 8325133 A | 12/1996 |
| JP | 10251371 A | 9/1998 |
| JP | 2003073700 A | 3/2003 |
| JP | 2003082397 A | 3/2003 |
| JP | 2004345983 A | 12/2004 |
| JP | 2005171063 A | 6/2005 |
| JP | 2007197540 A | 8/2007 |
| JP | 2007091954 A | 12/2007 |
| KR | 20020003442 | 1/2002 |
| WO | WO9514495 A1 | 6/1995 |
| WO | WO01/24770 A1 | 4/2001 |
| WO | WO 2004/032859 A | 4/2004 |
| WO | WO2004/041991 A1 | 5/2004 |
| WO | WO2005/003423 A1 | 1/2005 |
| WO | WO2007033598 A1 | 3/2007 |
| WO | WO2007/093558 A2 | 8/2007 |
| WO | WO2009019571 | 2/2009 |

OTHER PUBLICATIONS

P&G Case 11200M ISR dated May 6, 2011, PCT/US2009/067130, 5 pages.
P&G Case 11201M ISR dated May 4, 2011, PCT/US2009/067088, 5 pages.
P&G Case 11201M ISR dated Jul. 19, 2011, PCT/US2009/067088, 7 pages.
P&G Case 11202M3 ISR dated May 9, 2011, PCT/US2009/067132, 5 pages.
P&G Case 11202M2 ISR dated Jul. 20, 2011, PCT/US2009/067131, 5 pages.
P&G Case 11202M ISR dated Apr. 29, 2011, PCT/US2009/067089, 5 pages.
P&G Case 10997M ISR dated Jul. 15, 2009, PCT/IB2009/050388, 8 pages.
P&G Case 11037M ISR dated Aug. 17, 2009, PCT/US2009/040739, 6 pages.
P&G Case 11037M ISR dated Nov. 4, 2009, PCT/US2009/040739, 10 pages.
P&G Case 11199M ISR dated Dec. 15, 2011, PCT/US2009/067087, 5 pages.
P&G Case 11203M ISR dated Jul. 19, 2011, PCT/US2009/067133, 4 pages.
P&G Case 11200M ISR dated Jul. 19, 2011, PCT/US2009/067130, 7 pages.
P&G Case 11494M ISR dated Apr. 27, 2011, PCT/US2010/059365, 5 pages.
P&G Case 11495M ISR dated Apr. 27, 2011, PCT/US2010/059455, 5 pages.
P&G Case 11523M ISR dated Apr. 27, 2011, PCT/US2010/059359, 5 pages.
T. Hildebrand, P. Rüegsegger. "Quantification of bone microarchitecture with the structure model index." Computer Methods in Biomechanics and Biomedical Engineering 1997; 1:15-23.
Vesterby, A.; Star volume in bone research. A histomorphometric analysis of trabecular bone structure using vertical sections; Anat Rec.; Feb. 1993; 235(2): 325-334.
C. D. Vaughan. Solubility, Effects in Product, Package, Penetration and Preservation, Cosmetics and Toiletries, vol. 103, Oct. 1988.
*Encyclopedia of Polymer Science and Engineering*, vol. 15, 2d ed., pp. 204-308, John Wiley & Sons, Inc. (1989).
Anonymous: "P8136 Poly(vinyl alcohol)" Internet article, [Online] XP002538935 Retrieved from the Internet: URL:http://www.sigmaaldrich.com/catalog/ProductDetail.do?D7=0&N25=SEARCH_CONCAT_PNO%7CBRAND_KEY&N4=P8136%7CSIAL&N25=0&QS=0N&F=SPEC> [retrieved on Jul. 28, 2009].
*M. K. Industires* (Gujarat India, http://www.soapstrips.com).
*Sanipro Sanitary Products* (Italy, http://www.sanipro.it).
*Adhesives Research* (Pennsylvania, http://12.4.33.51/news/apresmed.htm).
*Solublon* (Toyohashi Japan, http://www.solublon.com).
*SPI Pharma* (Delaware, http://www.spipharma.com).
*Wenda* (China, http://www.wenda.com).
*MOVA Pharmaceutical and Kosmos* (USA, http://www.icon-pr.com/news/news_print.cfm?inv_id=266-1).
*Cima Labs, Inc.* (Minnesota, http://www.cimalabs.com/).
*Cardinal Health* (Dublin, Ohio, http://spd.cardinal.com/).
*Le Laboratoire du Bain* (France, http://www.labodubain.com/).
*Amerilab Technologies, Inc.* (Minnesota, http://www.amerilabtech.com/).
*Meguiar's Car Wash Strips*: (*Meguiar's Inc.* California, http://www.automotivedigest.com/view_art.asp.?articlesID=12414).
*Pure Soap Leafz*: (*Soap UNLTD*, Netherlands, http://www.upandunder.co.uk/eshop/catalogue/testbs.asp?Manufacturer_ID=252&Activity_ID=33&Description_ID=157).
*Dissolving Soap Strips* (*Ranir LLC*, Michigan, www.ranir.com).
*Japanese Paper Soap* (http://www.wishingfish.com/papersoap.html).
*Travelers Passport Paper Soap Sheets* (http://www.weddingfavorsnow.com/index.asp?PageAction=VIEWPROD&ProdID=510).
Office Action for U.S. Appl. No. 12/424,812 dated Nov. 1, 2011; P&G Case 11037M; Glenn, Jr. et al.; filed Apr. 16, 2009.
Office Action for U.S. Appl. No. 12/633,228 dated May 11, 2011; P&G Case 11199M; Glenn, Jr. et al.; filed Dec. 8, 2009.
Office Action for U.S. Appl. No. 12/633,228 dated Oct. 25, 2011; P&G Case 11199M; Glenn, Jr. et al.; filed Dec. 8, 2009.
Office Action for U.S. Appl. No. 12/633,257 dated Jun. 1, 2011; P&G Case 11200M; Glenn, Jr. et al.; filed Dec. 8, 2009.
Office Action for U.S. Appl. No. 12/633,257 dated Nov. 17, 2011; P&G Case 11200M; Glenn, Jr. et al.; filed Dec. 8, 2009.
Office Action for U.S. Appl. No. 12/633,550 dated Nov. 16, 2011; P&G Case 11202M; Glenn, Jr. et al.; filed Dec. 8, 2009.
Office Action for U.S. Appl. No. 12/633,335 dated Jul. 8, 2011; P&G Case 11202M2; Glenn, Jr. et al.; filed Dec. 8, 2009.
Office Action for U.S. Appl. No. 12/633,415 dated Nov. 14, 2011; P&G Case 11202M3; Glenn, Jr. et al.; filed Dec. 8, 2009.
Office Action for U.S. Appl. No. 12/633,572 dated Jul. 28, 2011; P&G Case 11203M; Glenn, Jr. et al.; filed Dec. 8, 2009.
Office Action for U.S. Appl. No. 12/361,634 dated Sep. 14, 2011; P&G Case 10997M; Glenn, Jr. et al.; filed Jan. 29, 2009.

* cited by examiner

Top Cross-Section | Middle Cross-Section | Bottom Cross-Section

Top Cross-Section | Middle Cross-Section | Bottom Cross-Section

Top Cross-Section | Middle Cross-Section | Bottom Cross-Section

Top Cross-Section | Middle Cross-Section | Bottom Cross-Section

Top Cross-Section　　Middle Cross-Section　　Bottom Cross-Section

Top Cross-Section　　Middle Cross-Section　　Bottom Cross-Section

Top Cross-Section　　Middle Cross-Section　　Bottom Cross-Section

Interior Volume        Full Volume

Interior Volume        Full Volume

Interior Volume

Full Volume

Interior Volume

Full Volume

Interior Volume        Full Volume

Interior Volume        Full Volume

Interior Volume                    Full Volume

Interior Volume                    Full Volume

Interior Volume Full Volume

Interior Volume Full Volume

PERSONAL CARE COMPOSITION IN THE FORM OF AN ARTICLE HAVING A POROUS, DISSOLVABLE SOLID STRUCTURE

CROSS REFERENCE TO RELATE APPLICATION

This application claims the benefit of U.S. Provisional Application Ser. No. 61/120,765 filed Dec. 8, 2008 which is incorporate by reference herein.

FIELD OF THE INVENTION

The present invention relates to personal care compositions, especially those personal care compositions in the form of an article that is a porous, dissolvable solid structure, delivering consumer desired lathering.

BACKGROUND OF THE INVENTION

The majority of personal care products in the market today are sold as liquid products. While widely used, liquid products have disadvantages in terms of packaging, storage, transportation, and convenience of use.

Liquid personal care products typically are sold in bottles which add significant cost as well as packaging waste, much of which ends up in land-fills. Liquid personal care products also usually comprise a substantial amount of water in the formula which adds significant weight and size translating into greater shipping and storage costs. Liquid personal care products can also be difficult to use in terms of controlling dosage and the delivery of the product.

Consumers using personal care products desire amounts of lather and dose or weight of the product adequate to wash the hair and/or body. However, to deliver this desired lather and dose a certain level of actives, in particular surfactants, is traditionally needed. High levels of actives are difficult to deliver in a personal care product that is in the form of a porous dissolvable solid structure, as the increase in actives can minimize the dissolution rate of the product. Therefore, a consumer would have to spend an undesirable amount of time waiting for the product to dissolve into a form which is usable for personal cleansing.

It is an object of the present invention to provide a dissolvable solid personal care product that can be conveniently and quickly dissolved in the palm of the consumer. Once dissolved the product constitutes a liquid product which results in ease of application to hair and/or skin and provides a consumer desirable level of lather and dose of product in their palm. It is a further object of the present invention to provide such a product that can be produced in an economical manner via physical aeration followed by drying.

Additionally, it is an object of the present invention to provide a dissolvable solid personal care product that can be conveniently and quickly dissolved in the palm of the consumer to constitute a liquid product for ease of application to hair/skin while providing sufficient topical delivery of active agents for whole head hair and whole body skin applications (with similar performance as today's liquid products).

SUMMARY OF THE INVENTION

A dissolvable article in the form of a porous dissolvable solid structure, comprising: from about 10% to about 50% water soluble polymer; from about 1% to about 25% plasticizer; from about 23% to about 75% surfactant; wherein the surfactants comprise one or more surfactants from Group I, wherein Group I includes anionic surfactants, and one or more surfactants from Group II, wherein Group II includes a surfactant selected from the group consisting of amphoteric, zwitterionic and combinations thereof; wherein the ratio of Group I to Group II surfactants is from about 95:5 to about 30:70; and wherein the dissolvable article has a density of from about 0.05 g/cm$^3$ to about 0.25 g/cm$^3$.

A pre-mix suitable for use in making a dissolvable article that is in the form of a porous dissolvable solid structure, wherein the pre-mix comprises: from about 3% to about 20% water soluble polymer; from about 0.3% to about 8% plasticizer; from about 8% to about 30% surfactant; wherein the surfactants comprise: one or more surfactants from Group I, wherein Group I includes anionic surfactants, and one or more surfactants from Group II, wherein Group II includes a surfactant selected from the group consisting of amphoteric, zwitterionic and combinations thereof; wherein the ratio of Group I to Group II surfactants is from about 95:5 to about 30:70; and wherein the pre-mix has from about 20% to about 50% solids, and a viscosity of from about 5,000 cps to about 150,000 cps.

A dissolvable article in the form of a porous dissolvable solid structure, wherein the article is formed by a process comprising the steps of: preparing a pre-mix, wherein the pre-mix comprises a surfactant, a water soluble polymer, a plasticizer, one or more surfactants from Group I, wherein Group I includes anionic surfactants, and one or more surfactants from Group II, wherein Group II includes a surfactant selected from the group consisting of amphoteric, zwitterionic and combinations thereof, and wherein the pre-mix has from about 20% to about 50% solids and a viscosity of from about 5,000 cps to about 150,000 cps; aerating the pre-mix by introducing a gas into the pre-mix to form a wet aerated pre-mix; forming the wet aerated pre-mix into a desired one or more shapes to form a shaped wet pre-mix; and forming the dissolvable article by drying the shaped wet pre-mix into a final moisture content, wherein the final moisture content is from about 0.1% to about 25% moisture.

BRIEF DESCRIPTION OF THE DRAWINGS

While the specification concludes with claims which particularly point out and distinctly claim the present invention, it is believed that the present invention will be better understood from the following description of embodiments, taken in conjunction with the accompanying drawings, in which like reference numerals identify identical elements and wherein:

DETAILED DESCRIPTION OF THE INVENTION

Figure 1A:
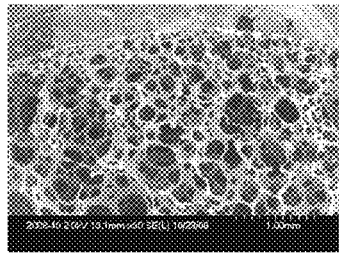
FIGS. 1A-1G are SEM images depicting the Dissolvable Article of the present invention.
Figure 1A:
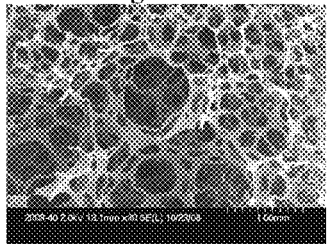
Figure 1A:
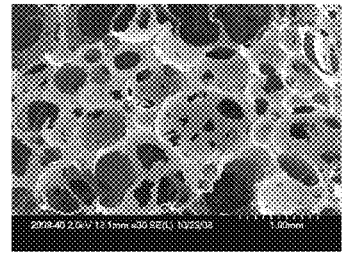
Figure 1B:
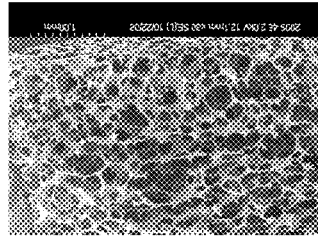
Figure 1B:
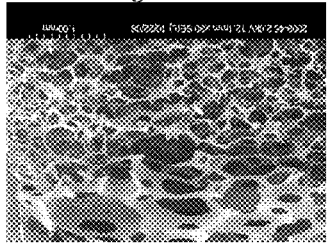
Figure 1B:
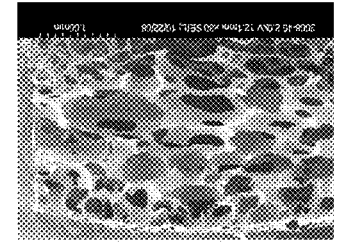
Figure 1C:
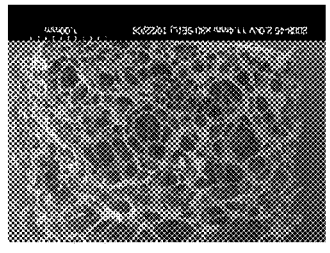
Figure 1C:
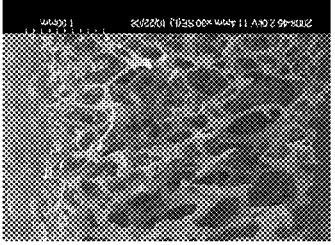
Figure 1C:
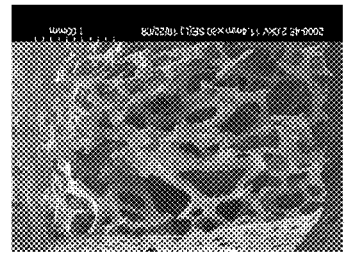
Figure 1D:
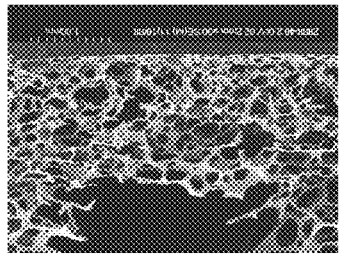
Figure 1D:
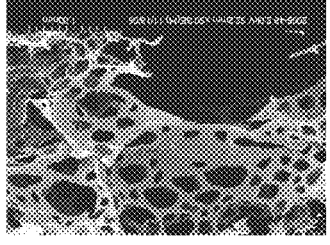
Figure 1D:
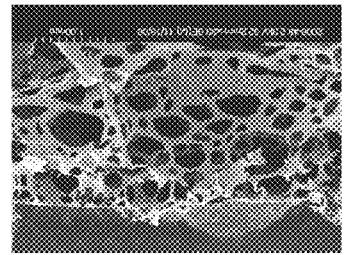
Figure 1E:
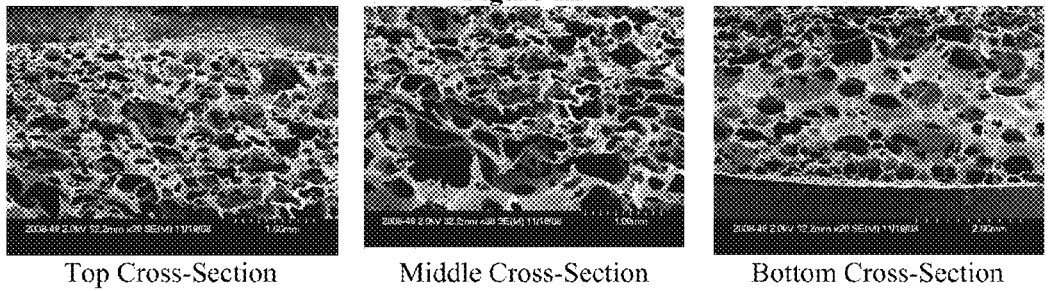
Figure 1F:
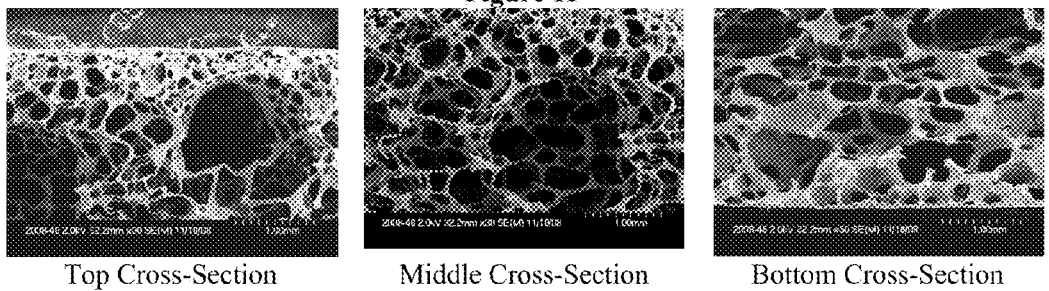
Figure 1G:
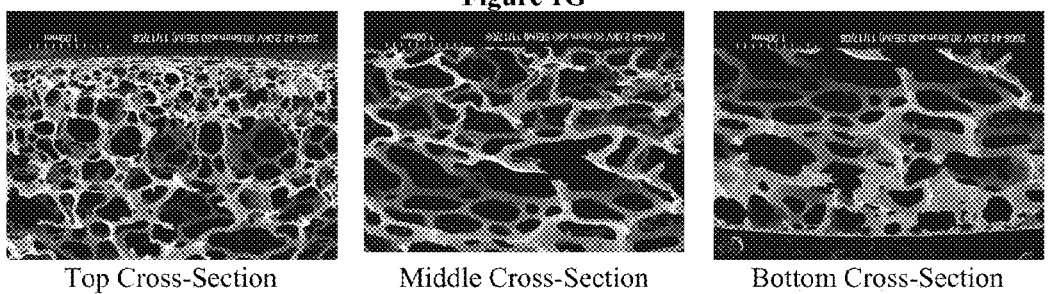

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

DEFINITIONS

The flexible porous dissolvable solid structure article may be referred to herein as "the Article" or "the Dissolvable Article". All references are intended to mean the flexible dissolvable porous solid structure article.

As used herein, "dissolvable" means that the flexible porous dissolvable solid structure article meets the hand dissolution value in order to be considered dissolvable within the context of this application.

Hand Dissolution Method: One pad with dimensions as specified in the examples (approximately 0.8 grams to 1.20 grams) of the dissolvable porous solid is placed in the palm of the hand while wearing nitrile gloves. 7.5 cm$^3$ of luke warm tap water (from about 30° C. to about 35° C.) is quickly applied to the product via syringe. Using a circular motion, palms of hands are rubbed together 2 strokes at a time until dissolution occurs (up to 30 strokes). The hand dissolution value is reported as the number of strokes it takes for complete dissolution or as 30 strokes as the maximum.

As used herein "porous solid structure" means a solid, interconnected, polymer-containing matrix that defines a network of spaces or cells that contain a gas, typically a gas such as air without collapse of the foam structure during the drying process, thereby maintaining the physical strength and cohesiveness of the solid.

To measure the Cell Wall Thickness and the cell interconnectivity via the Star Volume and the Structure Model Index, disk-like samples, approximately 4 cm in diameter and 3 to 7 mm high, are scanned using a micro computed tomography system (μICT80, SN 06071200, Scanco Medical AG). Each sample is imaged while sitting flat on the bottom of a cylindrical tube. Image acquisition parameters are 45 kVp, 177 μA, 51.2 mm field of view, 800 ms integration time, 1000 projections. The number of slices is adjusted to cover the height of the sample. The reconstructed data set consisted of a stack of images, each 2048×2048 pixels, with an isotropic resolution of 25 μm. For data analysis, a volume of interest is selected to be fully within the sample, avoiding the surface region. A typical volume of interest is 1028×772×98 voxels.

Cell Wall Thickness is measured according to the method defined for the measurement of Trabecular Thickness using Scanco Medical's Bone Trabecular Morphometry evaluation. The definition of Trabecular Thickness as taken from the Scanco User's manual: Trabecular Thickness uses a Euclidean distance transformation (EDM), which calculates the Euclidean distance from any point in the foreground to the nearest background point. The Trabecular Thickness measure represents twice the centerline values associated with the local maxima of the EDM, which represents the distance to the center of the object (twice this distance will yield the thickness).

Structure Model Index (SMI) is measured using Scanco Medical's Bone Trabecular Morphometry evaluation with a threshold of 17. With this index the structural appearance of trabecular bone is quantified (see T. Hildebrand, P. Rüegsegger. Quantification of bone microarchitecture with the structure model index. *Comp Meth Biomech Biomed Eng* 1997; 1:15-23). The triangulated surface is dilated in normal direction by an infinitesimal amount, and the new bone surface and volume is calculated. By this, the derivative of the bone surface (dBS/dr) can be determined. The SMI is then represented by the equation:

$$SMI = 6 \cdot \frac{BV \cdot \frac{dBS}{dr}}{BS^2}$$

SMI relates to the convexity of the structure to a model type. Ideal (flat) plates have an SMI of 0 (no surface change with dilation of the plates), whereas ideal cylindrical rods have an SMI of 3 (linear increase in surface with dilation of rods). Round spheres have an SMI of 4. Concave structure gives negative dBS/dr, resulting in negative SMI values. Artificial boundaries at the edge of the volume of interest are not included in the calculation and thus suppressed.

In addition to the Scanco Medical Analysis, StarVolume measurements are made. Star Volume is a measure of the "openness" of the void space in a two phase structure. By choosing a random uniformly distributed set of points in the phase of interest (in our case this is the background), we can extend lines in random directions from each of these points. The lines are extended until they touch the foreground phase. The length of each of these lines is then recorded. The random points have a sampling of 10 in each direction (x/y/z) and at each point 10 random angles are chosen. If the line extends to the border of the ROI of interest that line is discarded (we only want to accept lines that actually intersect with the foreground phase). The final equation is based upon the research published in *Star volume in bone research. A histomorphometric analysis of trabecular bone structure using vertical sections*; Vesterby, A.; Anat Rec.; 1993 February; 235(2):325-334:

$$StarVolume = \frac{4}{3}\pi \cdot \frac{\Sigma dist^3}{N}$$

where dist is the individual distances and N is the number of lines examined.

The Percent Open Cell Content is measured via gas pycnometry. Gas pycnometry is a common analytical technique that uses a gas displacement method to measure volume accurately. Inert gases, such as helium or nitrogen, are used as the displacement medium. The sample is sealed in the instrument compartment of known volume, the appropriate inert gas is admitted, and then expanded into another precision internal volume. The pressure before and after expansion is measured and used to compute the sample volume. Dividing this volume into the sample weight gives the gas displacement density.

ASTM Standard Test Method D2856 provides a procedure for determining the percentage of open cells using an older model of an air comparison pycnometer. This device is no longer manufactured. However, you can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials.

For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the true volume as measured by the Accupyc. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde On and Paul Webb.

The Specific Surface Area is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the degassed sample+sample tube weight. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved.

Sample Preparation (Degassing): A sample not adequately cleaned of adsorbed contaminants will outgas during an analysis and some portion of the surface will be inaccessible to measurement. The purpose of degassing is to remove these adsorbed molecules from the surface of the sample prior to analysis. Adsorptive molecules must reach all parts of the surface for the true surface area to be revealed. Samples are prepared by heating the sample while simultaneously evacuating the sample tube.

For these experiments, the samples are outgassed under evacuation at room temperature overnight. Samples may then analyzed using an ASAP 2420 with krypton gas adsorption. Krypton gas is preferred over nitrogen gas as it has a saturation pressure approximately 1/300 that of nitrogen at liquid nitrogen temperature (krypton: 2.5 torr; nitrogen: 760 torr). Therefore, compared to nitrogen, there is in the free space above the sample about 1/300 the number of krypton molecules present at the same relative pressure. Since about the same number of krypton and nitrogen molecules are required to form a monolayer, this number represents a far greater proportion of the quantity dosed than in the case of nitrogen. It is recommended that these measurements be conducted by Micromeretics Analytical Services, Inc. (One Micromeritics Dr, Suite 200, Norcross, Ga. 30093). More information on this technique is available on the Micromeretics Analytical Services web sites (www.particletesting.com or www.micromeritics.com), or published in a book, "Analytical Methods in Fine particle Technology", by Clyde Orr and Paul Webb.

The density of the Article is determined by the equation: Calculated Density=Basis Weight of Article/(Article Thickness×1,000). The Basis Weight and Thickness of the Article are determined in accordance with the methodologies described herein.

The thickness of the dissolvable porous solid (i.e., substrate or sample substrate) is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 psi (6.32 gm/cm$^2$).

The thickness of the dissolvable porous solid is measured by raising the platen, placing a section of the sample substrate on the stand beneath the platen, carefully lowering the platen to contact the sample substrate, releasing the platen, and measuring the thickness of the sample substrate in millimeters on the digital readout. The sample substrate should be fully extended to all edges of the platen to make sure thickness is measured at the lowest possible surface pressure, except for the case of more rigid substrates which are not flat. For more rigid substrates which are not completely flat, a flat edge of the substrate is measured using only one portion of the platen impinging on the flat portion of the substrate.

The Basis Weight, as used herein, means a basis weight calculated as the weight of the dissolvable porous solid component per area of the selected dissolvable porous solid (grams/m$^2$). The area is calculated as the projected area onto a flat surface perpendicular to the outer edges of the porous solid. For a flat object, the area is thus computed based on the area enclosed within the outer perimeter of the sample. For a spherical object, the area is thus computed based on the average diameter as $3.14 \times (diameter/2)^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (preferably shaded-in for contrast) including a scale and using image analysis techniques.

The density of the dissolvable porous solid is determined by the equation: Calculated Density=Basis Weight of porous solid/(Porous Solid Thickness×1,000). The Basis Weight and Thickness of the dissolvable porous solid are determined in accordance with the methodologies described herein.

The Scanning Electron Microscope (SEM) Imaging is performed by the following method: Representative sections are cut from the sponge with a clean razor blade and mounted with the cut face up on a standard cryo-SEM stub. Samples are secured onto the stub with carbon tape and silver paint. Samples are imaged using an Hitachi S-4700 FE-SEM fitted with a Gatan Alto 2500 cryo stage. Samples are cooled to −95 dC before imaging in the microscope. Samples are lightly coated with Platinum to reduce charging. Representative images are collected at 2 kV, 20 uA extraction voltage, ultra high resolution mode using the lower secondary electron detector. Long working distances are used to allow the entire sample to be imaged in one frame.

The Dissolvable Article

The present inventors have found that the Dissolvable Article can be prepared such that the Dissolvable Article can be conveniently and quickly dissolved in the palm of the consumer resulting in a liquid product. Once dissolved, this product can be used in a manner similar to a conventional liquid product, i.e. applied to the skin and/or hair. It has been found that such Dissolvable Article can now deliver the desired amount of lather and dose into the hand, while continuing to deliver a consumer acceptable rate of dissolution.

The Dissolvable Article has a hand dissolution value of from about 1 to about 30 strokes, in one embodiment from about 2 to about 25 strokes, in another embodiment from about 3 to about 20 strokes, and in still another embodiment from about 4 to about 15 strokes.

The Dissolvable Article has a maximum Cell Wall Thickness. The Article has a Cell Wall Thickness of from about from about 0.02 mm to about 0.15 mm, in one embodiment from about 0.025 mm to about 0.12 mm, in another embodiment from about 0.03 mm to about 0.09 mm, and in still another embodiment from about 0.035 mm to about 0.06 mm.

The Dissolvable Article has a minimum level of interconnectivity between the cells, which is quantified by both the Star Volume, the Structure Model Index (SMI), and the Percent Open Cell Content. The Dissolvable Article has a Star Volume of from about 1 $mm^3$ to about 90 $mm^3$, i, in one embodiment from about 1.5 $mm^3$ to about 60 $mm^3$, in another embodiment from about 2 $mm^3$ to about 30 $mm^3$, and in still another embodiment from about 2.5 $mm^3$ to about 15 $mm^3$. The Dissolvable Article has a non-negative Structure Model Index of from about 0.0 to about 3.0, in one embodiment from about 0.5 to about 2.75, and in another embodiment from about 1.0 to about 2.50. The Dissolvable Article has a Percent Open Cell Content of from about 80% to 100%, in one embodiment from about 85% to about 97.5%, and in another embodiment from about 90% to about 95%.

The Dissolvable Article also has a minimum Specific Surface Area. The Dissolvable Article has a Specific Surface Area of from about 0.03 $m^2/g$ to about 0.25 $m^2/g$, in one embodiment from about 0.035 $m^2/g$ to about 0.22 $m^2/g$, in another embodiment from about 0.04 $m^2/g$ to about 0.19 $m^2/g$, and in still another embodiment from about 0.045 $m^2/g$ to about 0.16 $m^2/g$.

In one embodiment the Dissolvable Article is a flat, flexible substrate in the form of a pad, a strip or tape and having a thickness of from about 0.5 mm to about 10 mm, in one embodiment from about 1 mm to about 9 mm, in another embodiment from about 2 mm to about 8 mm, and in a further embodiment from about 3 mm to about 7 mm as measured by the below methodology. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

The Dissolvable Article has a basis weight of from about 125 grams/$m^2$ to about 3,000 grams/$m^2$, in one embodiment from about 200 grams/$m^2$ to about 2,500 grams/$m^2$, in another embodiment from about 300 grams/$m^2$ to about 2,000 grams/$m^2$, and in still another embodiment from about 400 grams/$m^2$ to about 1,500 grams/$m^2$.

The Dissolvable Article has a dry density of from about 0.05 g/$cm^3$ to about 0.40 g/$cm^3$, in another embodiment from about 0.08 g/$cm^3$ to about 0.30 g/$cm^3$, and in yet another embodiment from about 0.10 g/$cm^3$ to about 0.25 g/$cm^3$, and in yet another embodiment from about 0.12 g/$cm^3$ to about 0.20 g/$cm^3$.

The Dissolvable Article has a BET Surface Area of from about 0.03 $m^2/g$ to about 0.25 $m^2/g$, in one embodiment from about 0.035 $m^2/g$ to about 0.22 $m^2/g$, in another embodiment from about 0.04 $m^2/g$ to about 0.19 $m^2/g$, and in another embodiment from about 0.045 $m^2/g$ to about 0.16 $m^2/g$.

Consumers desire a certain dose of liquid product to achieve sufficient lather and therefore, a desired amount of shampoo and/or skin cleaning composition. To deliver both a consumer acceptable lather and dose into the palm of the hand, it traditionally would be expected that a certain amount of solids, or particular solids density, would be included in the product. In particular, the desired lather is delivered via the surfactant present in the product. However, it has been found that the higher the solid density of the product (i.e. the higher the level of surfactant present in the product per unit volume), the slower the dissolution of the Dissolvable Article. A slow dissolution is undesirable for the consumer, as a consumer is unwilling to wait for an extended period of time for a Dissolvable Article to dissolve into a liquid product.

It has been surprisingly found that a synergy exists between anionic surfactants and amphoteric and/or zwitterionic surfactants, resulting in faster dissolution of the Dissolvable Article. Therefore, the desired level of surfactant can be delivered with a consumer acceptable rate of dissolution, if the Dissolvable Article comprises the surfactant blend of the present invention. The Dissolvable Article of the present invention comprises from about a 6.5% to about 71% weight % of dry solids of a Group I surfactant, and from about 1.0% to about 52.5% weight % of dry solids of a Group II surfactant. In another embodiment the Dissolvable Article of the present invention comprises from about 15% to about 50% weight % of dry solids of a Group I surfactant, and from about 10% to about 35% weight % of dry solids of a Group II surfactant. In another embodiment the Dissolvable Article of the present invention comprises from about 25% to about 40% weight % of dry solids of a Group I surfactant, and from about 15% to about 30% weight % of dry solids of a Group II surfactant.

The Dissolvable Article comprising the surfactant blend of the present invention delivers a higher rate of dissolution than a Dissolvable Article comprising surfactants outside the blend of the present invention. For example a dissolvable article prepared from a 0.32 wet density foam comprising only (Group I) anionic surfactant has a dissolution rate of greater than 30 strokes. Whereas the Dissolvable Article prepared from a 0.32 wet density foam comprising Group I and Group II surfactants at a ratio of 60:40 has a dissolution rate of 4 strokes. (See Examples 8.2 and 10.2 of Table 1) Additionally, these products have increased lathering, another consumer desirable attribute. For the same products described above (Examples 8.2 and 10.2 of Table 1) the lather volume increases from 85 ml for the product comprising Group I surfactants only, to 140 ml for the products which include Group I and Group II surfactants at a ratio of 60:40. Additionally, the Dissolvable Article prepared from a 0.32 wet density foam comprising Group I and Group II surfactants at a ratio of 80:20 exhibits dissolution and lather performance in-between the above two described Dissolvable Articles (See Example 9.2 of Table 1).

TABLE 1

Dissolution/Lather Performance from Higher Density Pads
(prepared from 0.32 wet density foams)

| Example | Anionic:Amphoteric Ratio | Amphoteric (Zwitterionic) | Anionic chain length | Hand Dissolution | Lather Volume |
|---|---|---|---|---|---|
| Ex. 8.2 | 100:0 | LAA | C11-12 | >30 strokes | 85 ml |
| Ex. 9.2 | 80:20 | LAA | C11-12 | 14 strokes | 110 ml |

TABLE 1-continued

Dissolution/Lather Performance from Higher Density Pads
(prepared from 0.32 wet density foams)

| Example | Anionic:Amphoteric Ratio | Amphoteric (Zwitterionic) | Anionic chain length | Hand Dissolution | Lather Volume |
|---|---|---|---|---|---|
| Ex. 10.2 | 60:40 | LAA | C11-12 | 4 strokes | 140 ml |
| Ex. 11.2 | 80:20 | CAPB | C11-12 | >30 strokes | 90 ml |
| Ex. 12.2 | 80:20 | LAPB | C11-12 | >30 strokes | 100 ml |
| Ex. 13.2 | 80:20 | LAA | C12[1] | 6 strokes | 95 ml |
| Ex. 14.2 | 80:20 | LAA | C12[2] | 10 strokes | 90 ml |

[1] 62.5/37.5 ratio of Ammonium Laureth-3 sulfate to Ammonium Lauryl Sulfate
[2] 37.5/62.5 ratio of Ammonium Laureth-3 sulfate to Ammonium Lauryl Sulfate The same benefits also exist for lower solids density Dissolvable Articles. For example dissolvable articles prepared from a 0.26 wet density foam comprising only Group I surfactants have a dissolution rate of 12 strokes and a lather volume of 100 ml. However, the Dissolvable Articles prepared from a 0.26 wet density foam comprising Group I and Group II surfactants at a ratio of 60:40 have a dissolution rate of 4 strokes and a lather volume of 150 ml. Additionally, the Dissolvable Articles prepared from a 0.26 wet density foam comprising Group I and Group II surfactants at a ratio of 80:20 has a dissolution rate and a lather volume in-between the above two described Articles (See Examples 8.1, 9.1 and 10.1 of Table 2).

TABLE 2

Dissolution/Lather Performance from Lower Density Pads
(prepared from 0.26 wet density foams)

| Example | Anionic:Amphoteric Ratio | Amphoteric (Zwitterionic) | Anionic chain length | Hand Dissolution | Lather Volume |
|---|---|---|---|---|---|
| Ex. 8.1 | 100:0 | LAA | C11-12 | 12 strokes | 100 ml |
| Ex. 9.1 | 80:20 | LAA | C11-12 | 10 strokes | 110 ml |
| Ex. 10.1 | 60:40 | LAA | C11-12 | 4 strokes | 150 ml |
| Ex. 11.1 | 80:20 | CAPB | C11-12 | 18 strokes | 110 ml |
| Ex. 12.1 | 80:20 | LAPB | C11-12 | 14 strokes | 115 ml |
| Ex. 13.1 | 80:20 | LAA | C12[1] | 6 strokes | 90 ml |
| Ex. 14.1 | 80:20 | LAA | C12[2] | 6 strokes | 90 ml |

[1] 62.5/37.5 ratio of Ammonium Laureth-3 sulfate to Ammonium Lauryl Sulfate
[2] 37.5/62.5 ratio of Ammonium Laureth-3 sulfate to Ammonium Lauryl Sulfate The measured structural parameters of all of the bulk porous solids at both the low and high densities are all within the ranges of the present invention and without consistent differences correlating to the measured dissolution performance (See Tables 3 and 4). Indeed, all of these solids are processed from similar processing conditions and wet densities giving rise to similar overall average open-celled architecture.

However, the measured structural parameters in Tables 3 and 4 represent the averaged values representing the entirety of the bulk solid and ignore potential regional variations. While not wishing to be bound by theory, it is believed that the surfactant blends of the present invention result in a less dense bottom solid layer (formed adjacent to the bottom of the mold) that has greater inter-connectivity between the pores. It is believed that the drying process results in generally increased density of the bottom region, resulting from gravity during the drying process, which mitigates water from entering the porous solid during use by the consumer; which significantly decreases the dissolution performance. For example, a Dissolvable Article prepared from a 0.26 wet density foam comprising only (Group I) anionic surfactant can be observed via SEM imaging. The SEM images reveal a bottom cross-sectional layer that is more dense than either the middle or top layers, and a Dissolvable Article with less interconnectivity between the pores (See FIG. 1A). Whereas a Dissolvable Article prepared from a 0.26 wet density foam comprising Group I and Group II surfactants at a ratio of 60:40 can be observed via SEM imaging to comprise a bottom cross-sectional layer that is less dense and with pores that are more interconnected (See FIG. 1C). Similarly, the Dissolvable Article prepared from a 0.26 wet density foam comprising Group I and Group II surfactants at a ratio of 80:20 can be observed via SEM imaging to comprise a bottom cross-sectional layer with a density and pore interconnectivity in-between that of the above described Articles (See FIG. 1B). FIGS. 1A-1G are SEM images of the products described as 8.1-14.1 in Table 2.

TABLE 3

Structural Characterization from Lower Density Pads
(prepared from 0.26 grams per cubic centimeter wet density foams)

| Example | Kr BET Surface Area (m²/g) | Pycnometry % Open Cells | Micro-CT Cell Wall thickness (mm) | Micro-CT Star Volume (mm³) | Micro-CT SMI Index | SEM Image | μCT Image |
|---|---|---|---|---|---|---|---|
| Ex. 8.1  | 0.096 | 91.0% | 0.041 | 7.5  | 2.3 | FIG. 5a | FIG. 6a |
| Ex. 9.1  | 0.047 | 90.7% | 0.050 | 11.1 | 2.4 | FIG. 5b | FIG. 6b |
| Ex. 10.1 | 0.051 | 92.0% | 0.062 | 5.7  | 2.4 | FIG. 5c | FIG. 6c |
| Ex. 11.1 | 0.059 | 89.8% | 0.044 | 1.6  | 2.4 | FIG. 5d | FIG. 6d |
| Ex. 12.1 | 0.059 | 93.6% | 0.045 | 5.7  | 2.2 | FIG. 5e | FIG. 6e |
| Ex. 13.1 | 0.150 | 94.4% | 0.049 | 7.0  | 2.5 | FIG. 5f | FIG. 6f |
| Ex. 14.1 | 0.133 | 93.6% | 0.052 | 7.0  | 2.4 | FIG. 5g | FIG. 6g |

TABLE 4

Structural Characterization from Lower Density Pads
(prepared from 0.32 grams per cubic centimer wet density foams)

| Example | Kr BET Surface Area (m²/g) | Pycnometry % Open Cells | Micro-CT Cell Wall thickness (mm) | Micro-CT Star Volume (mm³) | Micro-CT SMI Index | μCT Image |
|---|---|---|---|---|---|---|
| Ex. 8.2  | 0.095 | 89.1% | 0.044 | 8.5 | 2.2 | FIG. 7a |
| Ex. 9.2  | 0.044 | 90.6% | 0.047 | 4.4 | 2.5 | FIG. 7b |
| Ex. 10.2 | 0.049 | 92.4% | 0.060 | 7.2 | 2.4 | FIG. 7c |

Figure 2A:
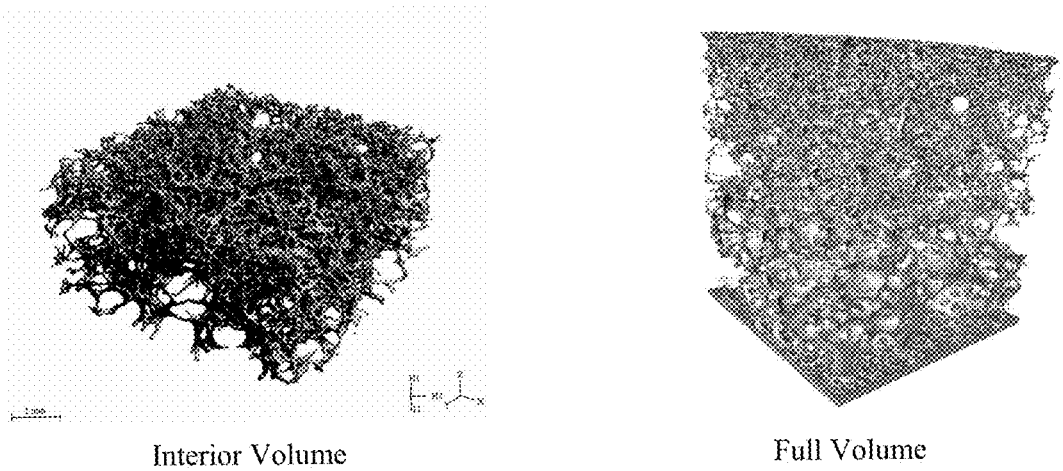
FIGS. 2A-2G are micro CT images depicting the Dissolvable Article of the present invention.
Figure 2B:
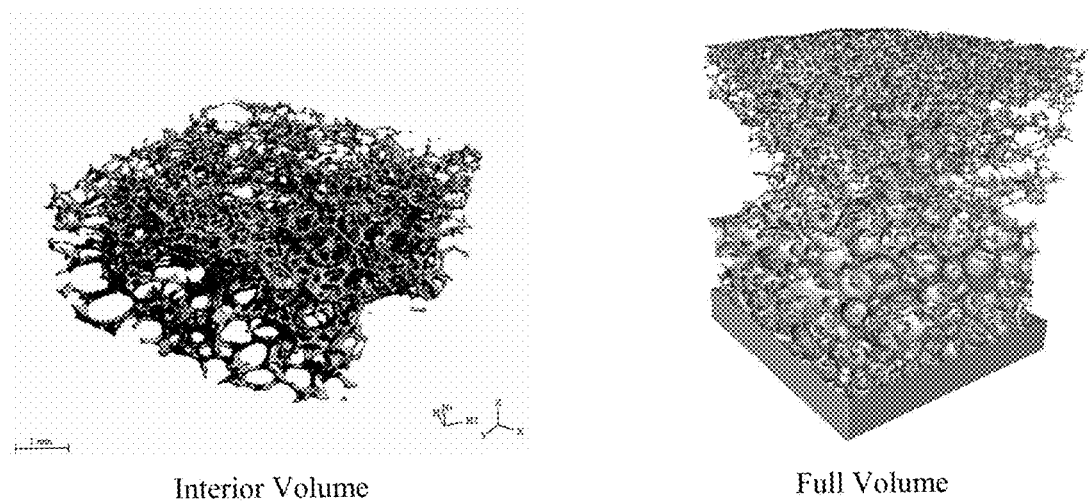
Figure 2C:
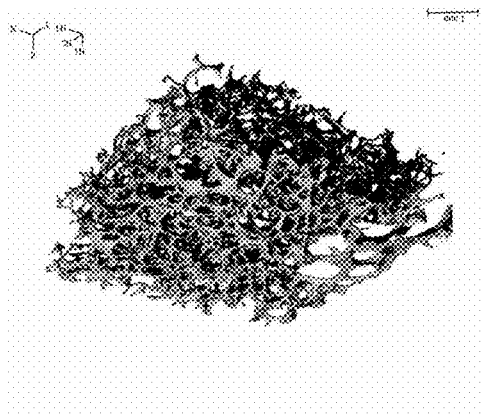
Figure 2C:
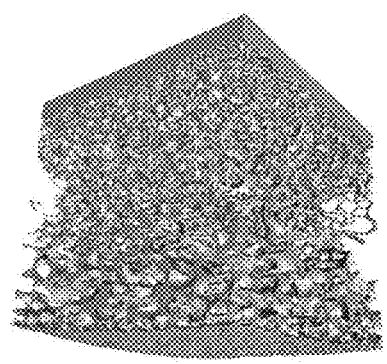
Figure 2D:
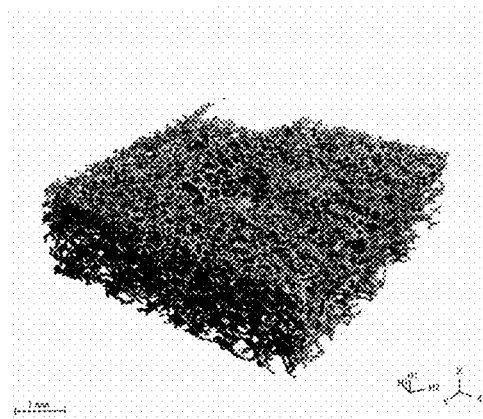
Figure 2D:
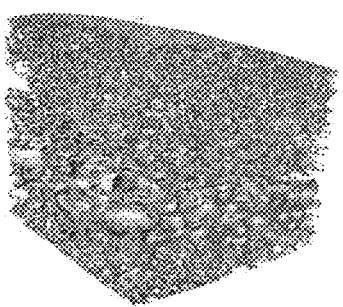
Figure 2E:
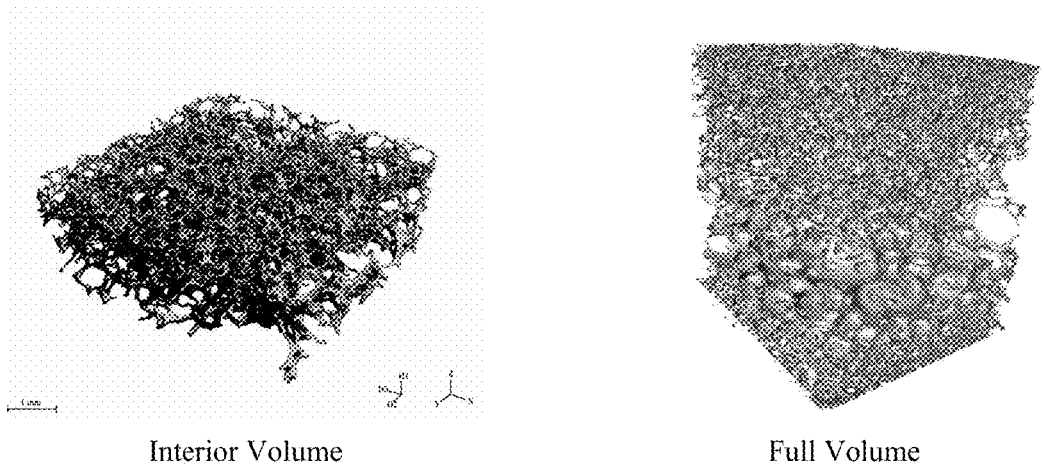
Figure 2F:
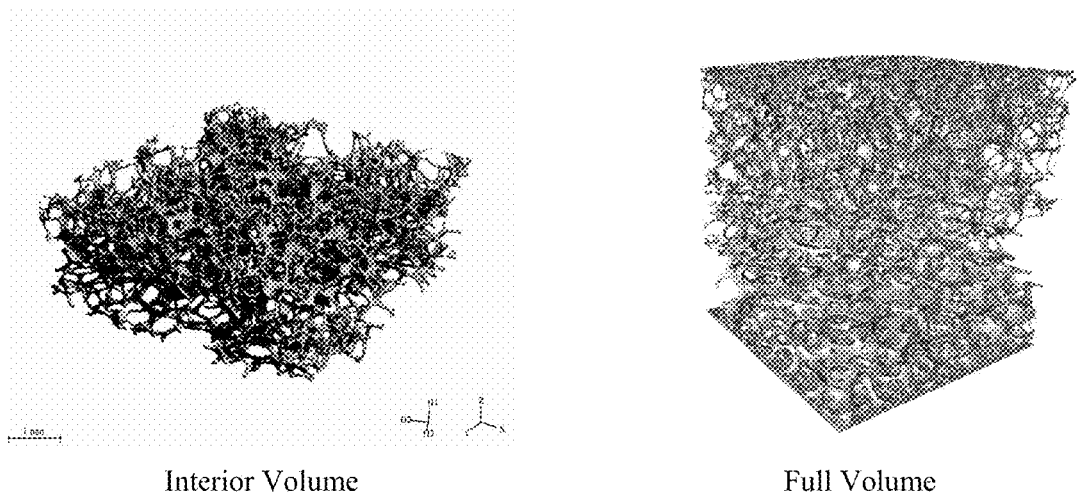
Figure 2G:
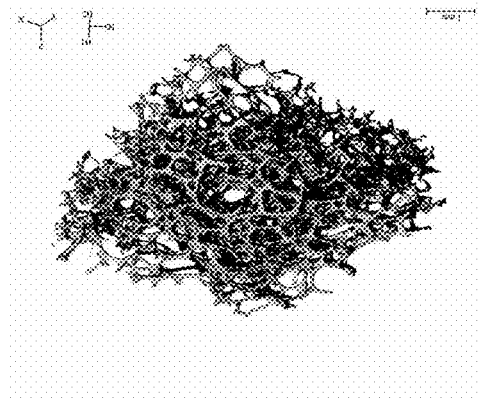
Figure 2G:
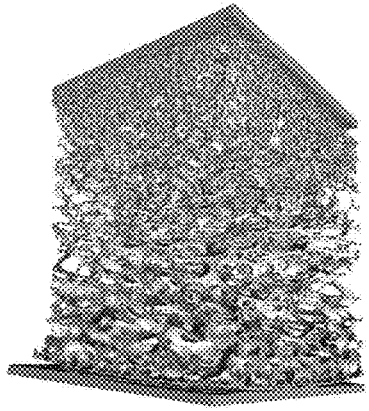
Figure 3A:
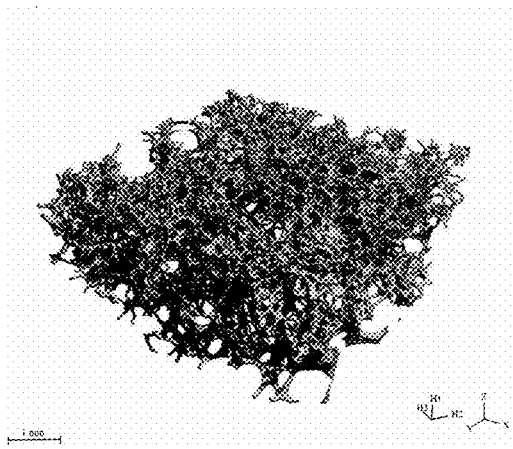
FIGS. 3A-3C are micro CT images depicting the Dissolvable Articles of the present invention.
Figure 3A:
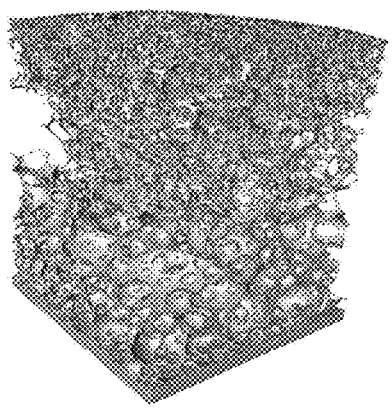
Figure 3B:
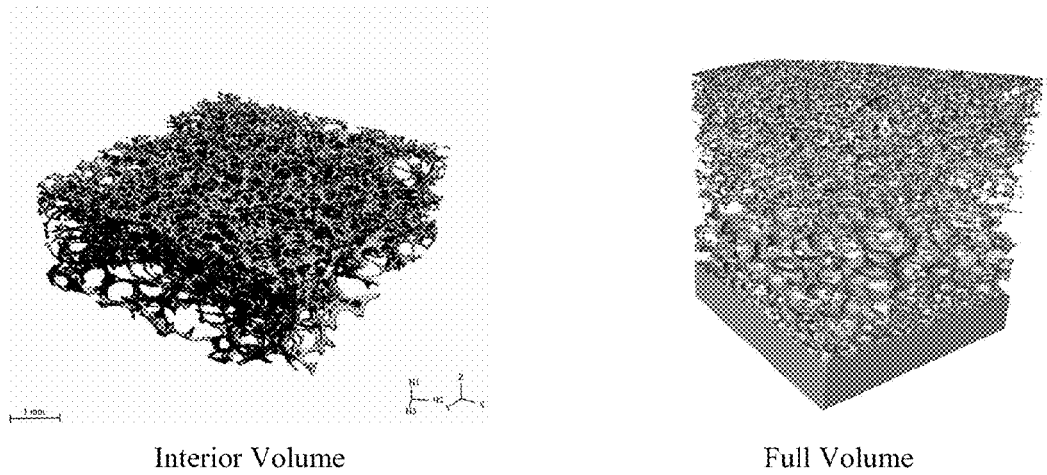
Figure 3C:
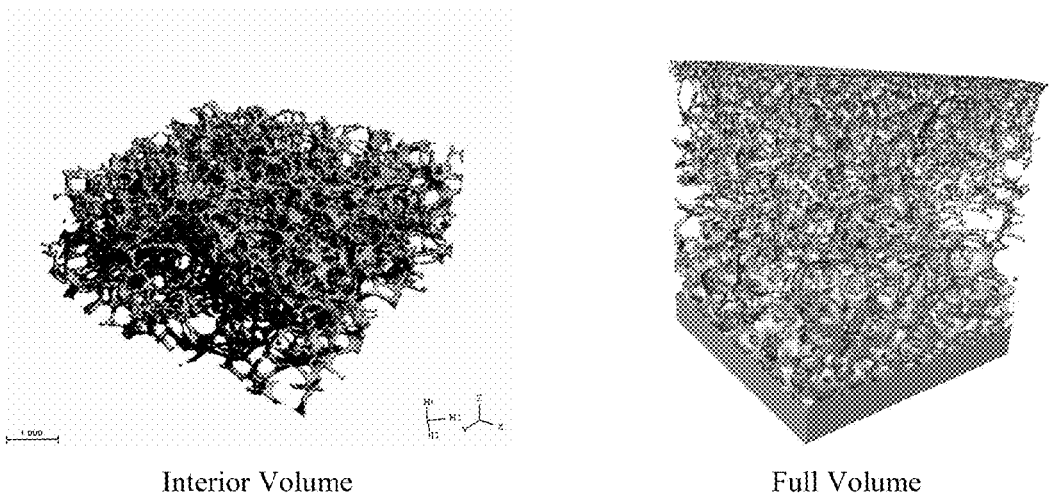

Similar observations can be made from Micro-CT images. Micro-CT images of Dissolvable Articles prepared from 0.26 and 0.32 wet density foams comprising i) Group I surfactants only are shown at FIGS. 2A and 3A, ii) Group I and Group II surfactants at a ratio of 60:40 are shown at FIGS. 2C and 3C, and iii) Group I and Group II surfactants at a ratio of 80:20 are shown at FIGS. 2B and 3B.

FIGS. 2A-2G are Micro CT images of the products described in Table 2 as 8.1-14.1. FIGS. 3A-3C are Micro CT images of the products described in Table 1 as 8.2-10.2.

Surfactant Blend

The Dissolvable Article of the present invention comprises from about 23% to about 75% of surfactant by weight of the total composition. In another embodiment, the Dissolvable Article comprises from about 50% to about 70% surfactant by weight of the total composition. The surfactant comprises a blend of Group I and Group II surfactants. The blend of surfactants of the present invention comprises one or more surfactants from Group I and one or more surfactants from Group II. Group I surfactants include anionic surfactants, and Group II surfactants include amphoteric surfactants, zwitterionic surfactants, and combinations thereof. In one embodiment of the present invention the ratio of Group I to Group II surfactants is from about 95:5 to about 30:70. In another embodiment of the present invention the ratio of Group I to Group II surfactants is from about 85:15 to about 40:60. In yet another embodiment of the present invention the ratio of Group I to Group II surfactants is from about 70:30 to about 55:45.

Group I Surfactants

The Group I surfactants of the present invention include one or more anionic surfactants. Suitable anionic surfactant components for use in the Dissolvable Article herein include those which are known for use in hair care or other personal care cleansing compositions. The concentration of the anionic surfactant component in the composition should be sufficient to provide the desired cleaning and lather performance, from about 6.5% to about 71% weight % of dry solids of a Group I surfactant.

Anionic surfactants suitable for use in the compositions include alkyl and alkyl ether sulfates. These materials have the respective formulae ROSO3M and RO(C2H4O)xSO3M, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Preferably, R has from about 8 to about 18 carbon atoms, more preferably from about 10 to about 16 carbon atoms, even more preferably from about 11 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Synthetic alcohols may include the grades available via Shell Chemical Co. under the NEODOL trade name as NEODOL 91 (C9-11 alcohols), NEODOL 23 (C12-13 alcohols), NEODOL 25 (C12-15 alcohols), NEODOL 45 (C14-15 alcohols), and NEODOL 135 (C11-C13-C15 alcohols). Lauryl alcohol and straight chain alcohols derived from coconut oil or palm kernel oil are preferred. Such alcohols are reacted with between about 0 and about 10, in one embodiment from about 2 to about 5, in another embodiment about 3, molar proportions of ethylene oxide, and the resulting mixture of molecular species having, for example, an average of 3 moles of ethylene oxide per mole of alcohol, is sulfated and neutralized.

Other suitable anionic surfactants are the water-soluble salts of organic, sulfuric acid reaction products conforming to the formula [R1-SO3-M] where R1 is a straight or branched chain, saturated, aliphatic hydrocarbon radical having from about 8 to about 24, preferably about 10 to about 18, carbon atoms; and M is a cation described hereinbefore.

Still other suitable anionic surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic surfactants suitable for use in the compositions are the succinnates, examples of which include disodium N-octadecylsulfosuccinnate; disodium laurylsulfosuccinate; diammonium laurylsulfosuccinate; tetrasodium N-(1, 2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the compositions are the beta-alkyloxy alkane sulfonates. These surfactants conform to the formula

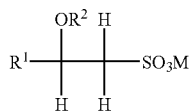

where R1 is a straight chain alkyl group having from about 6 to about 20 carbon atoms, R2 is a lower alkyl group having from about 1 to about 3 carbon atoms, preferably 1 carbon atom, and M is a water-soluble cation as described hereinbefore.

Additional anionic surfactants suitable for use in the compositions include ammonium lauryl sulfate, ammonium laureth sulfate, ammonium laureth-1 sulfate, ammonium laureth-2 sulfate, ammonium laureth-3 sulfate, triethanolamine lauryl sulfate, triethanolamine laureth sulfate, triethanolamine laureth-1 sulfate, triethanolamine laureth-2 sulfate, triethanolamine laureth-3 sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, monoethanolamine lauryl sulfate, sodium tridecyl benzene sulfonate, sodium dodecyl benzene sulfonate, sodium cocoyl isethionate, ammonium decyl sulfate, sodium decyl sulfate, ammonium undecyl sulfate, and ammonium undecyl sulfate and combinations thereof.

In one embodiment of the present invention, one or more of the surfactants is an alkyl sulfate. In one embodiment the one or more alkyl sulfates has an average moles of ethoxylation of from about 0.0 to about 1.9, in another embodiment the one or more alkyl sulfates has an average moles of ethoxylation of from about 0.0 to about 1.5, and in yet another embodiment the one or more alkyl sulfates has an average moles of ethoxylation of from about 0.0 to about 1.0. In one embodiment the one or more alkyl sulfates comprises an ammonium counter ion. Suitable examples of such surfactants with an ammonium counter ion include, but are not limited to, ammonium lauryl sulfate, ammonium laureth-1 sulfate, ammonium laureth-2 sulfate, and combinations thereof.

In one embodiment, one or more Group I surfactants are selected from alkyl sulfates with the following structure:

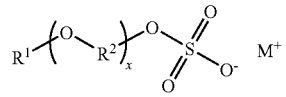

wherein $R^1$ is selected from C-linked monovalent substituents selected from the group consisting of substituted or unsubstituted, straight or branched alkyl or unsaturated alkyl systems comprising an average of 9.0 to 11.9 carbon atoms; $R^2$ is selected from the group consisting of C-linked divalent straight or branched alkyl systems comprising 2 to 3 carbon atoms; $M^+$ is a monovalent counterion selected from sodium, ammonium or protonated triethanolamine; and x is 0.0 to 3.0. In one embodiment, one or more of the alkyl sulfate surfactants according to the above structure comprise an average moles of ethoxylation of from about 0.0 to about 1.9, in another embodiment the alkyl sulfate surfactants according to the above structure comprise an average moles of ethoxylation of from about 0.0 to about 1.5, and in yet another embodiment the alkyl sulfate surfactants according to the above structure comprise an average moles of ethoxylation of from about 0.0 to about 1.0. Suitable examples include ammonium decyl sulfate, sodium decyl sulfate, ammonium undeceyl sulfate, sodium undecyl sulfate, triethanolamine decyl sulfate, or triethanolamine undecyl sulfate. In one embodiment the anionic surfactant of the present invention includes ammonium undecyl sulfate.

Group II Surfactants

The Group II surfactants of the present invention include one or more amphoteric surfactants, zwitterionic surfactants, and/or combinations thereof. Suitable amphoteric or zwitterionic surfactants for use in the composition herein include those which are known for use in hair care or other personal care cleansing. Concentration of such amphoteric surfactants, zwitterionic surfactants and/or combinations thereof, range from about 1.0% to about 52.5% weight % of dry solids. Non limiting examples of suitable zwitterionic or amphoteric surfactants are described in U.S. Pat. Nos. 5,104,646 (Bolich Jr. et al.), 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable examples of such amphoteric surfactants include, but are not limited to, sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium caprylo-amphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and combinations thereof.

In one embodiment, the amphoteric surfactant is a surfactant according to the following structure:

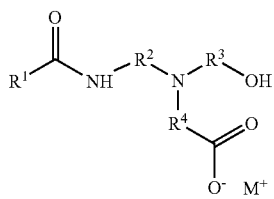

wherein R1 is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; R2, R3, and R4 are each independently selected from the group consisting of C-linked divalent straight alkyl systems comprising 1 to 3 carbon atoms, and C-linked divalent branched alkyl systems comprising 1 to 3 carbon atoms; and M+ is a monovalent counterion selected from the group consisting of sodium, ammonium and protonated triethanolamine. Specific examples of suitable surfactants include sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, and triethanolamine cocoamphoacetate.

Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Suitable zwitterionic surfactants include, but are not limited to, cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and combinations thereof.

Optional Surfactants

The compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

Water-Soluble Polymer ("Polymer Structurant")

The present invention comprises water-soluble polymer that functions as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have a solubility in water, measured at 25° C., of from about 0.1 gram/liter (g/L), to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The terms "water-soluble polymer" and "polymer structurant" are used interchangeably herein. Furthermore, whenever the singular term "polymer" is stated, it should be understood that the term is broad enough to include one polymer or a mixture of more than one polymer. For instance, if a mixture of polymers is used, the polymer solubility as referred to herein would refer to the solubility of the mixture of polymers, rather than to the solubility of each polymer individually.

The one or more water-soluble polymers of the present invention are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous solid.

The water-soluble polymer(s) of the present invention can include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, copolymers of acrylic acid and methyl methacrylate, polyethylene glycol monomethacrylates, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, and combinations thereof.

The water-soluble polymer(s) of the present invention may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers are also useful as water-soluble polymer(s) in the present invention. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

Suitable water-soluble polymers of the present invention include polyvinyl alcohols, polyvinylpyrrolidones, polyalkylene oxides, starch and starch derivatives, pullulan, gelatin, hydroxypropylmethylcelluloses, methycelluloses, and carboxymethycelluloses.

More preferred water-soluble polymers of the present invention include polyvinyl alcohols, and hydroxypropylmethylcelluloses. Suitable polyvinyl alcohols include those available from Celanese Corporation (Dallas, Tex.) under the Celvol trade name including, but not limited to, Celvol 523, Celvol 530, Celvol 540, Celvol 518, Celvol, 513, Celvol 508, Celvol 504, and combinations thereof. Suitable hydroxypropylmethylcelluloses include those available from the Dow Chemical Company (Midland, Mich.) under the Methocel trade name including, but not limited, to Methocel E50, Methocel E15, Methocel E6, Methocel E5, Methocel E3, Methocel F50, Methocel K100, Methocel K3, Methocel A400, and combinations thereof including combinations with above mentioned hydroxypropylmethylcelluloses.

In a particular embodiment, the above mentioned water-soluble polymer(s) of the present invention may be blended with any single starch or combination of starches as a filler material in such an amount as to reduce the overall level of water-soluble polymers required, so long as it helps provide the dissolvable porous solid with the requisite structure and physical/chemical characteristics as described herein. In such instances, the combined weight percentage of the water-soluble polymer(s) and starch-based material generally ranges from about 10% to about 40 wt %, in one embodiment from about 12 to about 30%, and in a particular embodiment from about 15% to about 25% by weight relative to the total weight of the porous solid. The weight ratio of the water-soluble polymer(s) to the starch-based material can generally range from about 1:10 to about 10:1, in one embodiment from about 1:8 to about 8:1, in still another embodiment from about 1:7 to about 7:1, and in yet another embodiment from about 6:1 to about 1:6.

Typical sources for starch-based materials of the present invention can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof.

The starch-based materials of the present invention may also include native starches that are modified using any modification known in the art, including physically modified starches examples of which include sheared starches or thermally-inhibited starches; chemically modified starches including those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof; conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

Plasticizer

The porous dissolvable solids of the present invention comprise a water soluble plasticizing agent suitable for use in personal care compositions. Non-limiting examples of suitable plasticizing agents include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Examples of polycarboxylic acids include, but are not limited to citric acid, maleic acid, succinic acid, polyacrylic acid, and polymaleic acid. Examples of suitable polyesters include, but are not limited to, glycerol triacetate, acetylated-monoglyceride, diethyl phthalate, triethyl citrate, tributyl citrate, acetyl triethyl citrate, acetyl tributyl citrate. Examples of suitable dimethicone copolyols include, but are not limited to, PEG-12 dimethicone, PEG/PPG-18/18 dimethicone, and PPG-12 dimethicone. Other suitable platicizers of the present invention include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of C2-C10 alcohols and acids); and any other water soluble plasticizer known to one skilled in the art of the foods and plastics industries; and mixtures thereof. Preferred placticizers include glycerin and propylene glycol. European Patent Number EP283165B1 discloses other suitable plasticizers, including glycerol derivatives such as propoxylated glycerol.

Optional Ingredients

The Article may further comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials.

Product Form

The Dissolvable Article of the present invention can be produced in any of a variety of product forms, including dissolvable porous solids used alone or in combination with other personal care components. The dissolvable porous solids can be continuous or discontinuous when used in the personal care compositions. Regardless of the product form, the key to all of the product form embodiments contemplated within the scope of the method of the present invention is the selected and defined dissolvable porous solid that comprises a combination of a solid polymeric structurant and a surfactant-containing active ingredient, all as defined herein.

The Dissolvable Article of the present invention are preferably in the form of one or more flat sheets or pads of an adequate size to be able to be handled easily by the user. It may have a square, rectangle or disc shape or any other shape. The pads can also be in the form of a continuous strip including delivered on a tape-like roll dispenser with individual portions dispensed via perforations and or a cutting mechanism. Alternatively, the dissolvable porous solids of the present invention are in the form of one or more cylindrical objects, spherical objects, tubular objects or any other shaped object. The dissolvable porous solids of the present invention can have a thickness (caliper) of from about 0.5 mm to about 10 mm, in one embodiment from about 1 mm to about 7 mm, and in still another embodiment from about 2 mm to about 6 mm. In the case of cylindrical, spherical, or other objects with more of a third dimension versus a pad or strip, the thickness is taken as the maximum distance of the shortest dimension, i.e., the diameter of a sphere or cylinder for instance.

The Dissolvable Article of the present invention may comprise one or more textured, dimpled or otherwise topographically patterned surfaces including letters, logos or figures. The textured substrate preferably results from the shape of the substrate, in that the outermost surface of the substrate contains portions that are raised with respect to other areas of the surface. The raised portions can result from the formed shape of the article, for example the article can be formed originally in a dimpled or waffle pattern. The raised portions can also be the result of creping processes, imprinted coatings, embossing patterns, laminating to other layers having raised portions, or the result of the physical form of the dissolvable porous solid substrate itself. The texturing can also be the result of laminating the substrate to a second substrate that is textured.

In a particular embodiment, the Dissolvable Article of the present invention can be perforated with holes or channels penetrating into or through the porous solid. These perforations can be formed during the drying process via spikes extended from the surface of the underlying mold, belt or other non-stick surface. Alternatively, these perforations can be formed after the drying process via poking or sticking the porous solids with pins, needles or other sharp objects. Preferably, these perforations are great in number per surface area, but not so great in number so as to sacrifice the integrity or physical appearance of the porous solid. It has been found that such perforations increase the dissolution rate of the porous solids into water relative to un-perforated porous solids.

The Dissolvable Article of the present invention can also be delivered via a water insoluble implement or device. For instance, they may be attached or glued by some mechanism to an applicator to facilitate application to hair and/or skin, i.e., a comb, rag, wand, or any other conceivable water-insoluble applicator. Additionally, the dissolvable porous solids may be adsorbed to the surfaces a separate high surface area water-insoluble implement, i.e., a porous sponge, a puff, a flat sheet etc. For the latter, the Dissolvable Article of the present invention may be adsorbed as a thin film or layer.

Product Types

Non-limiting examples of product type embodiments for use by the Dissolvable Article and methods of the present invention include hair conditioning substrates, moisturizing substrates, other hair treatment substrates, other skin or body treatment substrates, shaving preparation substrates, pet care substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, fragrance-containing substrates, and the like.

Method of Manufacture

The dissolvable articles of the present invention can be prepared by the process comprising: (1) Preparing a processing mixture comprising surfactant(s), dissolved polymer structurant, plasticizer and other optional ingredients; (2) Aerating the mixture by introducing a gas into the mixture; (3) Forming the aerated wet mixture into a desired one or more shapes; and (4) Drying the aerated wet mixture to a desired final moisture content (e.g., from about 0.1 to 25% moisture, by addition of energy).

Preparation of Processing Mixture

The processing mixture is generally prepared by dissolving the polymer structurant in the presence of water, plasticizer and other optional ingredients by heating followed by cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the surfactant(s), the plasticizer, and other optional ingredients including stepwise processing via pre-mix portions of any combination of ingredients.

The processing mixtures of the present invention comprise: from about 20% to about 50% solids, in one embodiment from about 25% to about 45% solids, and in another embodiment from about 30% to about 40% solids, by weight of the processing mixture before drying; and have a viscosity of from about 5000 cps to about 150,000 cps, in one embodiment from about 7,500 cps to about 125,000 cps, in another embodiment from about 10,000 cps to about 100,000 cps, and in still another embodiment from about 12,500 cps to about 75,000 cps. The processing mixture viscosity values can be measured on a suitable rheometer, such as a TA Instruments AR500 Rheometer with 4.0 cm diameter parallel plate and 1,200 micron gap at a shear rate of 1.0 reciprocal seconds for a period of 30 seconds at 25° C. (available from TA Instruments, New Castle, Del.), or on a standard viscometer, such as a Brookfield Model DV-1 PRIME Digital Viscometer with CP-41 and CP-42 spindles at a shear rate of 1.0 reciprocal seconds for a period of 2 minutes at 25° C. (available from Brookfield Engineering Laboratories, Inc., Middleboro, Mass.). The % solids content is the summation of the weight percentages by weight of the total processing mixture of all of the solid, semi-solid and liquid components excluding water and any obviously volatile materials such as low boiling alcohols.

Aeration of Processing Mixture

The aeration of the processing mixture is accomplished by introducing a gas into the mixture, preferably by mechanical mixing energy but also may be achieved via chemical means. The aeration may be accomplished by any suitable mechanical processing means, including but not limited to: (i) Batch tank aeration via mechanical mixing including planetary mixers or other suitable mixing vessels, (ii) semi-continuous or continuous aerators utilized in the food industry (pressurized and non-pressurized), or (iii) spray-drying the processing mixture in order to form aerated beads or particles that can be compressed such as in a mould with heat in order to form the porous solid.

In a particular embodiment, it has been discovered that the dissolvable porous solids of the present invention can be prepared within semi-continuous and continuous pressurized aerators that are conventionally utilized within the foods industry in the production of marshmallows. Suitable pressurized aerators include the Morton whisk (Morton Machine Co., Motherwell, Scotland), the Oakes continuous automatic mixer (E.T. Oakes Corporation, Hauppauge, N.Y.), the Fedco Continuous Mixer (The Peerless Group, Sidney, Ohio), and the Preswhip (Hosokawa Micron Group, Osaka, Japan).

The aerated processing mixtures of the present invention (prior to drying) have a wet density of from about 0.15 g/cm$^3$ to about 0.50 g/cm$^3$, in one embodiment from about 0.20 g/cm$^3$ to about 0.45 g/cm$^3$, in another embodiment from about 0.25 g/cm$^3$ to about 0.40 g/cm$^3$, and in yet another embodiment from about 0.30 g/cm$^3$ to about 0.35 g/cm$^3$.

Forming the Aerated Wet Processing Mixture

The forming of the aerated wet processing mixture may be accomplished by any suitable means to form the mixture in a desired shape or shapes including, but not limited to (i) depositing the aerated mixture to specially designed moulds comprising a non-interacting and non-stick surface including Teflon, metal, HDPE, polycarbonate, neoprene, rubber, LDPE, glass and the like; (ii) depositing the aerated mixture into cavities imprinted in dry granular starch contained in a shallow tray (Starch moulding forming technique widely utilized in the confectionery industry); and (iii) depositing the aerated mixture onto a continuous belt or screen comprising any non-interacting or non-stick material Teflon, metal, HDPE, polycarbonate, neoprene, rubber, LDPE, glass and the like which may be later stamped, cut, embossed or stored on a roll.

Drying the Formed Aerated Wet Processing Mixture

The drying of the formed aerated wet processing mixture may be accomplished by any suitable means including, but not limited to: (i) drying room(s) including rooms with controlled temperature and pressure or atmospheric conditions; (ii) ovens including non-convection or convection ovens with controlled temperature and optionally humidity; (iii) Truck/Tray driers, (iv) multi-stage inline driers; (v) impingement ovens; (vi) rotary ovens/driers; (vii) inline roasters; (viii) rapid high heat transfer ovens and driers; (ix) dual plenum roasters, (x) conveyor driers, (xi) microwave drying technology, and combinations thereof. Preferably, any suitable drying means that does not comprise freeze-drying can be used.

Optional ingredients may be imparted during any of the above described four processing steps or even after the drying process.

The dissolvable porous solids of the present invention may also be prepared with chemical foaming agents by in-situ gas formation (via chemical reaction of one or more ingredients, including formation of $CO_2$ by an effervescent system). Alternatively, the dissolvable porous solids may be prepared with volatile blowing agents (low boiling hydrocarbon solvents such as isopentane, hexane and the like).

Methods of Use

The Dissolvable Article of the present invention may be used for treating mammalian keratinous tissue such as hair and/or skin, and provide rapid rinse-ability. The method for conditioning the hair may comprise the steps of: a) applying an effective amount of the dissolvable porous solid to the hand, b) wetting the dissolvable porous solid with water and rubbing to dissolve the solid, c) applying the dissolved material to either the hair or skin such as to treat, and d) rinsing the diluted treatment from the hair or skin using water. These steps can be repeated as many times as desired to achieve the desired treatment benefit.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams per dose, preferably from about 0.7 grams to about 5 grams per dose, and more preferably from about 0.9 grams to about 3 grams per dose.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Examples 1-7

Surfactant/Polymer Liquid Processing Compositions

The following surfactant/polymer liquid processing compositions are prepared at the indicated weight percentages as described below. The liquid formulations differ on the ratio of anionic:amphoteric surfactant, the type of amphoteric surfactant, and the type of anionic surfactants:

| Component | Ex. 1 | Ex. 2 | Ex. 3 | Ex. 4 |
|---|---|---|---|---|
| Anionic:Amphoteric (Zwitterionic) Ratio | 100:0 | 80:20 | 60:40 | 80:20 |
| Glycerin[1] | 3.0 | 3.0 | 3.0 | 3.0 |
| Polyvinyl alcohol[2] | 7.4 | 7.4 | 7.4 | 7.4 |
| Sodium Lauroamphoacetate (26% activity)[3] | 0.0 | 14.6 | 29.2 | 0.0 |
| Cocamidopropyl betaine (31% activity)[4] | 0.0 | 0.0 | 0.0 | 12.3 |
| Lauramidopropyl betaine (34% activity)[5] | 0.0 | 0.0 | 0.0 | 0.0 |
| Ammonium Laureth-3 sulfate (25% activity)[6] | 7.5 | 6.0 | 4.5 | 6.0 |
| Ammonium undecyl sulfate (24% activity)[7] | 30.3 | 24.3 | 18.2 | 24.3 |
| Ammonium Laureth-1 sulfate (70% activity)[8] | 12.1 | 9.7 | 7.2 | 9.7 |
| Ammonium Lauryl sulfate (25% activity)[9] | 0.0 | 0.0 | 0.0 | 0.0 |
| Citric Acid[10] | 0.04 | 0.6 | 1.0 | 0.0 |
| Distilled water | 39.7 | 34.4 | 29.5 | 37.3 |
| Total | 100.0 | 100.0 | 100.0 | 100.0 |
| pH | 6.1 | 6.4 | 6.1 | 6.5 |
| Viscosity (cp) | 5,300 | 8,200 | 12,800 | 11,200 |

[1]Superol K, USP FCC EP Glycerin, supplier: Procter & Gamble Chemicals
[2]Sigma-Aldrich Catalog No. 363081, MW 85,000-124,000, 87-89% hydrolyzed
[3]MACKAM HPL-28ULS, supplier: McIntyre Group Ltd, University Park, IL,
[4]AMPHOSOL HCA-B, supplier: Stepan Company, Northfield, IL.
[5]MACKAM DAB-ULS, supplier: McIntyre Group Ltd, University Park, IL.
[6]Ammonium Laureth-3 Sulfate at 25% active with an estimated C8/C9/C10/C11/C12/C13/C14/C15/C16/C18 alkyl chain length distribution of 0/0.3/0.9/0.5/71.5/1/20/1.9/3.9/0 and an average of 2.0 moles of ethoxylation, supplier: Procter & Gamble Chemicals
[7]Ammonium Undecyl Sulfate at 24% active with an estimated C8/C9/C10/C11/C12/C13/C14/C15/C16/C18 alkyl chain length distribution of 0/0/0.6/93.6/5.1/0.7/0/0/0/0, supplier: Procter & Gamble Chemicals
[8]Ammonium Laureth-1 Sulfate at 70% active with an estimated C8/C9/C10/C11/C12/C13/C14/C15/C16/C18 alkyl chain length distribution of 0/0.3/1.3/0.5/69.6/1.1/21.8/1.2/4.2/0 and an average of 0.82 moles of ethoxylation, supplier: Procter & Gamble Chemicals
[9]Ammonium Lauryl Sulfate at 25% active with an estimated C8/C9/C10/C11/C12/C13/C14/C15/C16/C18 alkyl chain length distribution of 0/0.3/1.1/0.5/70.6/1.1/20.9/1.6/4.1/0, supplier: Procter & Gamble Chemicals
[10]Citric Acid Anhydrous Fine Granular 51N, supplier: S.A. Citrique Belge N.V. Pastorijstraat 249, B-3300 Tienen, Belgium

| Component | Ex. 5 | Ex. 6 | Ex. 7 |
|---|---|---|---|
| Anionic:Amphoteric (Zwitterionic) Ratio | 80:20 | 80:20 | 80:20 |
| Glycerin[1] | 3.0 | 3.0 | 3.0 |
| Polyvinyl alcohol[2] | 7.4 | 7.4 | 7.4 |
| Sodium Lauroamphoacetate (26% activity)[3] | 0.0 | 14.2 | 14.2 |
| Cocamidopropyl betaine (31% activity)[4] | 0.0 | 0.0 | 0.0 |
| Lauramidopropyl betaine (34% activity)[5] | 11.2 | 0.0 | 0.0 |
| Ammonium Laureth-3 sulfate (25% activity)[6] | 6.0 | 32.0 | 19.2 |
| Ammonium undecyl sulfate (24% activity)[7] | 24.3 | 0.0 | 0.0 |
| Ammonium Laureth-1 sulfate (70% activity)[8] | 9.7 | 0.0 | 0.0 |
| Ammonium Lauryl sulfate (25% activity)[9] | 0.0 | 19.2 | 32.0 |
| Cetyl alcohol[10] | 0.0 | 0.7 | 0.7 |
| Cocamide MEA[11] | 0.0 | 1.2 | 1.2 |
| Citric Acid[12] | 0.00 | 0.6 | 1.0 |
| Distilled water | 38.4 | 21.7 | 21.3 |
| Total | 100.0 | 100.0 | 100.0 |
| pH | 5.6 | 6.5 | 6.5 |
| Viscosity (cp) | 8,600 | 7,500 | 13,800 |

[1]Superol K, USP FCC EP Glycerin, supplier: Procter & Gamble Chemicals
[2]Sigma-Aldrich Catalog No. 363081, MW 85,000-124,000, 87-89% hydrolyzed
[3]MACKAM HPL-28ULS, supplier: McIntyre Group Ltd, University Park, IL,
[4]AMPHOSOL HCA-B, supplier: Stepan Company, Northfield, IL.
[5]MACKAM DAB-ULS, supplier: McIntyre Group Ltd, University Park, IL.
[6]Ammonium Laureth-3 Sulfate at 25% active with an estimated C8/C9/C10/C11/C12/C13/C14/C15/C16/C18 alkyl chain length distribution of 0/0.3/0.9/0.5/71.5/1/20/1.9/3.9/0 and an average of 2.0 moles of ethoxylation, supplier: Procter & Gamble Chemicals
[7]Ammonium Undecyl Sulfate at 24% active with an estimated C8/C9/C10/C11/C12/C13/C14/C15/C16/C18 alkyl chain length distribution of 0/0/0.6/93.6/5.1/0.7/0/0/0/0, supplier: Procter & Gamble Chemicals
[8]Ammonium Laureth-1 Sulfate at 70% active with an estimated C8/C9/C10/C11/C12/C13/C14/C15/C16/C18 alkyl chain length distribution of 0/0.3/1.3/0.5/69.6/1.1/21.8/1.2/4.2/0 and an average of 0.82 moles of ethoxylation, supplier: Procter & Gamble Chemicals
[9]Ammonium Lauryl Sulfate at 25% active with an estimated C8/C9/C10/C11/C12/C13/C14/C15/C16/C18 alkyl chain length distribution of 0/0.3/1.1/0.5/70.6/1.1/20.9/1.6/4.1/0, supplier: Procter & Gamble Chemicals
[10]CO-1694 CETYL ALCOHOL NF, supplier: Procter & Gamble Chemicals
[11]NINOL COMF, supplier: Stepan Company, Northfield, IL.
[12]Citric Acid Anhydrous Fine Granular 51N, supplier: S.A. Citrique Belge N.V. Pastorijstraat 249, B-3300 Tienen, Belgium A target weight of 300 grams, for each of the above compositions, is prepared with the use of a conventional overhead stirrer (IKA® RW20DZM Stirrer available from IKA® Works, Inc., Wilmington, Del.) and a hot plate (Corning Incorporated Life Sciences, Lowell, Mass.). Into an appropriately sized and cleaned vessel, the distilled water and glycerin are added with stirring at 100-150 rpm until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 75 to 80 C after which surfactants are added. The mixture is then heated to 85 C while continuing to stir and then allowed to cool to room temperature. Additional distilled water is added to compensate for water lost to evaporation (based on the original tare weight of the container). The final pH is between 5.2-6.6 and adjusted with citric acid or diluted sodium hydroxide if necessary. The resulting processing mixture viscosity is measured.

Examples 8-14

Dissolving Porous Shampoo Solids Comprising Different Surfactant Systems and Densities The dissolving porous shampoo solid Examples 8, 9, 10, 11, 12, 13 and 14 are prepared from the surfactant/polymer liquid processing solutions from Examples 1, 2, 3, 4, 5, 6, and 7, respectively, as described below. In the table, Na lauroamphoacetate is represented as LAA, cocamidopropyl betaine as CAPB and lauramidopropylbetaine as LAPB.

250 grams of the surfactant/polymer liquid processing solution (from Examples 1 through 7) is transferred into a 5 quart stainless steel bowl of a KitchenAid® Mixer Model K5SS (available from Hobart Corporation, Troy, Ohio) and fitted with a flat beater attachment. The mixture is vigorously aerated at a maximum speed setting of 10 until a wet density of approximately 0.26 grams per cubic centimeter or 0.32 grams per cubic centimeter is achieved (times recorded in table). The density is measured by weighing a filling a cup with a known volume and evenly scraping off the top of the cup with a spatula. The resulting aerated mixture is then spread with a spatula into square 160 mm×160 mm aluminum molds with a depth of 6.5 mm with the excess wet foam being removed with the straight edge of a large metal spatula that is held at a 45 degrees angle and slowly dragged uniformly across the mold surface. The aluminum molds are then placed into a 130 C convection oven for approximately 35 to 45 minutes or until the weight loss due to evaporation is between 67% and 69% of the original foam weight within each mold. The molds are allowed to cool to room temperature with the substantially dry porous solids removed from the molds with the aid of a thin spatula and tweezers.

|  | Ex. 8.1 | Ex. 8.2 | Ex. 9.1 | Ex. 9.2 |
|---|---|---|---|---|
| Anionic:Amphoteric (Zwitterionic) | 100:0 | 100:0 | 80:20 | 80:20 |
| Amphoteric (Zwitterionic) Surfactant | None | None | LAA | LAA |
| Anionic Surfactant Chain Lengths | C11-12 | C11-12 | C11-12 | C11-12 |
| Wet Density (g/cm$^3$) | 0.26 | 0.32 | 0.26 | 0.32 |
| Aeration Time (sec) | 35 | 25 | 75 | 65 |
| Average dry pad weight (g) | 0.87 | 1.03 | 0.94 | 1.08 |
| Average dry pad thickness (cm) | 0.53 | 0.52 | 0.53 | 0.49 |
| Average dry pad density (g/cm$^3$) | 0.10 | 0.12 | 0.10 | 0.13 |
| Average basis weight (g/m$^2$) | 520 | 610 | 560 | 640 |

|  | Ex. 10.1 | Ex. 10.2 | Ex. 11.1 | Ex. 11.2 |
|---|---|---|---|---|
| Anionic:Amphoteric (Zwitterionic) | 60:40 | 60:40 | 80:20 | 80:20 |
| Amphoteric (Zwitterionic) Surfactant | LAA | LAA | CAPB | CAPB |
| Anionic Surfactant Chain Lengths | C11-12 | C11-12 | C11-12 | C11-12 |
| Wet Density (g/cm$^3$) | 0.26 | 0.32 | 0.26 | 0.32 |
| Aeration Time (sec) | 125 | 95 | 90 | 65 |
| Average dry pad weight (g) | 0.95 | 1.11 | 0.87 | 1.10 |
| Average dry pad thickness (cm) | 0.52 | 0.50 | 0.46 | 0.50 |
| Average dry pad density (g/cm$^3$) | 0.11 | 0.13 | 0.11 | 0.13 |
| Average basis weight (g/m$^2$) | 560 | 660 | 510 | 650 |

|  | Ex. 12.1 | Ex. 12.2 |
|---|---|---|
| Anionic:Amphoteric (Zwitterionic) | 80:20 | 80:20 |
| Anionic Surfactant Chain Lengths | C11-12 | C11-12 |
| Amphoteric (Zwitterionic) Surfactant | LAPB | LAPB |
| Wet Density (g/cm$^3$) | 0.26 | 0.32 |
| Aeration Time (sec) | 45 | 40 |
| Average dry pad weight (g) | 0.88 | 1.09 |
| Average dry pad thickness (cm) | 0.51 | 0.51 |
| Average dry pad density (g/cm$^3$) | 0.10 | 0.13 |
| Average basis weight (g/m$^2$) | 520 | 640 |

|  | Ex. 13.1 | Ex. 13.2 | Ex. 14.1 | Ex. 14.2 |
|---|---|---|---|---|
| Anionic:Amphoteric (Zwitterionic) | 80:20 | 80:20 | 80:20 | 80:20 |
| Anionic Surfactant Chain Lengths | C12$^1$ | C12$^1$ | C12$^2$ | C12$^2$ |
| Amphoteric (Zwitterionic) Surfactant | LAA | LAA | LAA | LAA |
| Wet Density (g/cm$^3$) | 0.26 | 0.32 | 0.26 | 0.32 |
| Aeration Time (sec) | 60 | 44 | 105 | 85 |
| Average dry pad weight (g) | 0.86 | 1.02 | 0.89 | 1.02 |
| Average dry pad thickness (cm) | 0.53 | 0.60 | 0.54 | 0.60 |
| Average dry pad density (g/cm$^3$) | 0.10 | 0.10 | 0.10 | 0.10 |
| Average basis weight (g/m$^2$) | 510 | 620 | 520 | 600 |

$^1$62.5/37.5 ratio of Ammonium Laureth-3 sulfate to Ammonium Lauryl Sulfate
$^2$37.5/62.5 ratio of Ammonium Laureth-3 sulfate to Ammonium Lauryl Sulfate Each of the resulting 160 mm×160 mm square pads is cut into nine 43 mm×43 mm squares (with rounded edges) using a cutting die and a Samco SB20 cutting machine (each square representing surface area of approximately 16.9 square centimeters). The resulting smaller pads are then equilibrated overnight in a constant environment room kept at 70 degrees Fahrenheit and 50% relative humidity within large zip-lock bags that are left open to the room atmosphere. Each pad is then weighed and placed on an individual weight boat with the original mold side facing downward. The average pad weights are recorded.

Note that any actives and/or compositions disclosed herein can be used in and/or with the articles, and in particular the household care articles, disclosed in the following U.S. patent applications, including any publications claiming priority thereto: U.S. 61/229,981; U.S. 61/229,986; U.S. 61/229,990; U.S. 61/229,996; U.S. 61/230,000; and U.S. 61/230,004. Such articles may comprise one or more of the following: detersive surfactant; plasticizer; enzyme; suds suppressor; suds booster; bleach; bleach stabilizer; chelant; cleaning solvent; hydrotrope; divalent ion; fabric softener additive (e.g. quaternary ammonium compounds); nonionic surfactant; perfume; and/or a perfume delivery system. Such articles may be utilized in methods including, but not limited to: dosing into a washing machine to clean and/or treat fabric; dosing into a dishwasher to clean and/or treat cutlery; and dosing into water to clean and/or treat fabric and/or hard surfaces.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable article in the form of a porous dissolvable solid structure, comprising:
   a. from about 10% to about 50% water soluble polymer;
   b. from about 1% to about 25% plasticizer;
   c. from about 23% to about 75% surfactant; wherein said surfactants comprise:
      i. one or more surfactants from Group I, wherein Group I includes anionic surfactants, and
      ii. one or more surfactants from Group II, wherein Group II includes a surfactant selected from the group consisting of amphoteric, zwitterionic and combinations thereof;
   wherein the ratio of Group I to Group II surfactants is from about 95:5 to about 30:70; and wherein said dissolvable article has a density of from about 0.05 g/cm$^3$ to 0.25 g/cm$^3$, and wherein said dissolvable article has a % open cell content of from about 80% to about 100%, and wherein all percentages are weight percentages based on the total weight of said dissolvable article, and wherein all ratios are weight ratios.

2. The dissolvable article of claim 1, wherein said Group II surfactant is an amphoteric surfactant according to the following structure:

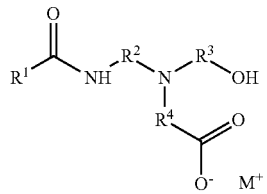

wherein $R^1$ is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; $R^2$, $R^3$, and $R^4$ are each independently selected from the group consisting of C-linked divalent straight alkyl systems comprising 1 to 3 carbon atoms, and C-linked divalent branched alkyl systems comprising 1 to 3 carbon atoms; and $M^+$ is a monovalent counterion selected from the group consisting of sodium, ammonium and protonated triethanolamine.

3. The dissolvable article of claim 1, wherein said Group II surfactant is an amphoteric surfactant selected from the group consisting of sodium lauroamphoacetate, sodium cocoamphoacetate, ammonium lauroamphoacetate, and ammonium cocoamphoacetate.

4. The dissolvable article of claim 1, wherein said Group II surfactant is an amphoteric surfactant selected from the group consisting of sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanolamine cocaminopropionate, triethanolamine cocaminodipropionate, triethanolamine cocoamphoacetate, triethanolamine cocoamphohydroxypropylsulfonate, triethanolamine cocoamphopropionate, triethanolamine cornamphopropionate, triethanolamine lauraminopropionate, triethanolamine lauroamphoacetate, triethanolamine lauroamphohydroxypropylsulfonate, triethanolamine lauroamphopropionate, triethanolamine cornamphopropionate, triethanolamine lauriminodipropionate, cocoamphodipropionic acid, disodium caproamphodiacetate, disodium caproamphodipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and combinations thereof.

5. The dissolvable article of claim 1, wherein said Group II surfactant is a zwitterionic surfactant selected from the group consisting of cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and combinations thereof.

6. The dissolvable article of claim 1, wherein the anionic surfactant is selected from the group consisting of an alkyl sulfate and an alkyl ether sulfate.

7. The dissolvable article of claim 6, wherein the alkyl sulfate comprises an ammonium counterion.

8. The dissolvable article of claim 7, wherein said alkyl sulfate is selected from the group consisting of ammonium lauryl sulfate, ammonium laureth-1 sulfate, ammonium laureth-2 sulfate, and ammonium laureth-3 sulfate.

9. The dissolvable article of claim 1, wherein said anionic surfactant is an alkyl sulfate according to the following structure:

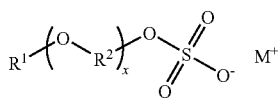

wherein $R^1$ is a C-linked monovalent substituent selected from the group consisting of substituted alkyl systems comprising an average of from 9 to 11.9 carbon atoms, unsubstituted alkyl systems comprising an average of from 9 to 11.9 carbon atoms, straight alkyl systems comprising an average of from 9 to 11.9 carbon atoms, branched alkyl systems comprising an average of from 9 to 11.9 carbon atoms, and unsaturated alkyl systems comprising an average of from 9 to 11.9 carbon atoms; $R^2$ is selected from the group consisting of C-linked divalent straight alkyl systems comprising 2 to 3 carbon atoms, and C-linked divalent branched alkyl systems comprising 2 to 3 carbon atoms; $M^+$ is a monovalent counterion selected from a group consisting of sodium, ammonium and protonated triethanolamine; and x is 0 to 3.

10. The dissolvable article of claim 1, wherein the anionic surfactant is selected from the group consisting of ammonium decyl sulfate, sodium decyl sulfate, ammonium undecyl sulfate, and ammonium undecyl sulfate.

11. The dissolvable article of claim 1, wherein the anionic surfactants is ammonium undecyl sulfate.

12. The dissolvable article of claim 1, wherein the ratio of Group I surfactants to Group II surfactant is from about 85:15 to about 40:60.

13. The dissolvable article of claim 1, wherein the ratio of Group I surfactants to Group II surfactant is from about 80:20 to about 50:50.

14. The dissolvable article of claim 1, wherein the ratio of Group I surfactants to Group II surfactant is from about 70:30 to about 55:45.

15. The dissolvable article of claim 1, wherein said water soluble polymer has a weighted average molecular weight of from about 40,000 to about 500,000.

16. The dissolvable article of claim 1, wherein said article is a non-freeze-dried article.

17. The dissolvable article of claim 1, comprising from about 20% to about 30% water soluble polymer.

18. The dissolvable article of claim 1, comprising from about 5% to about 15% plasticizer.

19. The dissolvable article of claim 1, comprising from about 50% to about 70% surfactants.

20. The dissolvable article of claim 1, wherein the density is about 0.075 g/cm$^3$ to about 0.20 g/cm$^3$.

21. The dissolvable article of claim 1 having a basis weight of from about 125 grams/m$^2$ to about 3,000 grams/m$^2$.

22. The dissolvable article of claim 1, having a basis weight of from about 150 grams/m$^2$ to about 1,200 grams/m$^2$.

23. The dissolvable article of claim 1, wherein said dissolvable article has a % open cell content of from about 85% to about 97.5%.

24. The dissolvable article of claim 23, wherein said dissolvable article has a % open cell content of from about 90% to about 95%.

25. The dissolvable article of claim 1, wherein said dissolvable article has a surface area of from about 0.03 m$^2$/g to about 0.25 m$^2$/g.

26. The dissolvable article of claim 25, wherein said dissolvable article has a surface area of from about 0.035 m$^2$/g to about 0.22 m$^2$/g.

27. The dissolvable article of claim 1, wherein said dissolvable article has a thickness of from about 0.5 to about 10 mm.

28. A dissolvable article in the form of a porous dissolvable solid structure, wherein said article is formed by a process comprising the steps of:
  a. preparing a pre-mix, wherein said pre-mix comprises a surfactant, a water soluble polymer, a plasticizer, one or more surfactants from Group I, wherein Group I includes anionic surfactants, and one or more surfactants from Group II, wherein Group II includes a surfactant selected from the group consisting of amphoteric, zwitterionic and combinations thereof, wherein the ratio of Group I to Group II surfactants is from about 95:5 to about 30:70, and wherein said pre-mix has from about 20% to about 50% solids and a viscosity of from about 5,000 cps to about 150,000 cps, wherein said percentages are weight percentages based on the total weight of said pre-mix, and wherein all ratios are weight ratios;
  b. aerating said pre-mix by introducing a gas into said pre-mix to form a wet aerated pre-mix;
  c. forming the wet aerated pre-mix into a desired one or more shapes to form a shaped wet pre-mix; and
  d. forming said dissolvable article by drying said shaped wet pre-mix into a final moisture content, wherein said final moisture content is from about 0.1% to about 25% moisture, wherein said dissolvable article comprises from about 23% to about 75% surfactant, wherein said dissolvable article has a density of from about 0.05 g/cm$^3$ to 0.25 g/cm$^3$, and wherein said dissolvable article has a % open cell content of from about 80% to about 100%, and wherein said percentages are weight percentages based on the total weight of said dissolvable article.

* * * * *